United States Patent [19]

Abraham et al.

[11] 3,959,263

[45] May 25, 1976

[54] PROSTAGLANDIN INTERMEDIATE

[75] Inventors: Nedumparambil A. Abraham, Dollard des Ormeaux; Jehan F. Bagli, Kirkland; Tibor Bogri, Montreal, all of Canada

[73] Assignee: American Home Products Corporation, New York, N.Y.

[22] Filed: June 19, 1974

[21] Appl. No.: 480,788

[52] U.S. Cl. .................... 260/240 R; 260/247.2 R; 260/268 R; 260/293.65; 260/326.2; 260/343.3 R; 260/346.2 R; 260/410.9 R; 260/413; 260/448.8 R; 260/468 D; 260/468 K; 260/501.1; 260/501.15; 260/501.17; 260/514 D; 424/305; 424/317; 424/318
[51] Int. Cl.² .................... C07C 61/38; C07C 69/74
[58] Field of Search ........ 260/468 D, 468 K, 240 R, 260/448.8 R

[56] References Cited
UNITED STATES PATENTS 3,849,474 11/1974 Abraham et al. ................. 260/468

Primary Examiner—Robert Gerstl

[57] ABSTRACT

Prostaglandin derivatives of the formula

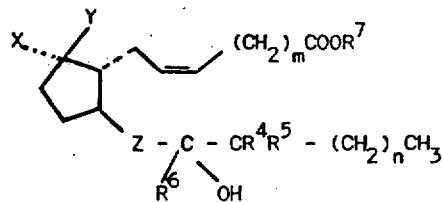

in which $R^4$, $R^5$, $R^6$ and $R^7$ each are hydrogen or lower alkyl, X is hydroxy and Y is hydrogen or X and Y together are oxo, Z is $CH_2CH_2$ or trans $CH=CH$, $m$ is an integer from one to three and $n$ is an integer from two to five, with the proviso that at least one of $R^4$, $R^5$ or $R^6$ is hydrogen, are disclosed together with a process for their preparation. The compounds in which Z is $CH_2CH_2$ and the process are new. The new derivatives possess hypotensive, antihypertensive, bronchospasmolytic, gastric acid secretion inhibiting, abortifacient, estrus synchronizing and ovulation regulating properties. These compounds also inhibit the aggregation of platelets and promote the disaggregation of aggregated platelets. Methods for their use are also disclosed.

5 Claims, No Drawings

PROSTAGLANDIN INTERMEDIATE

BACKGROUND OF THE INVENTION

1. Field of Invention

This invention relates to prostaglandin derivatives. More specifically this invention relates to 9,15-dioxygenated derivatives of prost-5-enoic and prosta-5,13-dienoic acid having optional alkyl substituents, to lower alkyl esters thereof and to homologs thereof. Also encompassed within this invention are processes for preparing these compounds and intermediates used therein.

2. Description of the Prior Art

The chemistry and pharmacological effects of the prostaglandins have been the subject of several recent reviews; for example, see E. W. Horton, Physiol. Rev., 49, 122 (1969), J. F. Bagli in "Annual Report in Medicinal Chemistry, 1969", C. K. Cain, Ed., Academic Press, New York and London, 1970, p. 170, and J. E. Pike in "Progress in the Chemistry of Organic Natural Products", Vol. 28, W. Herz, et al. Eds., Springer Verlag, New York, 1970, p. 313.

Due to the increasing interest in these natural products a rather extensive effort has been given recently to the synthesis of prostaglandins and their analogs. Included among these syntheses are several synthetic methods for the preparation of 9,15-dioxygenated derivatives of prostanoic or prost-13-enoic acid. For example, the synthesis of the first pharmacologically active 9,15-dioxygenated prostanoic acid derivative, 9$\beta$,15$\xi$-dihydroxyprost-13-enoic acid (11-desoxyprostaglandin F$_1$ $_\beta$) was reported in detail by J. F. Bagli, T. Bogri and R. Deghenghi, *Tetrahedron Letters*, 465 (1966). A significant simplification and modification of that process was described by Bagli and Bogri in U.S. Pat. No. 3,455,992, issued July 15, 1969, whereby 9$\beta$,15$\xi$-dihydroxyprost-13-enoic acid as well as homologs thereof were obtained, see also Bagli and Bogri, *Tetrahedron Letters*, 5 (1967).

Further improvements in the synthesis of 9,15-dioxygenated derivatives of prostanoic acid have been described by Bagli and Bogri in *Tetrahedron Letters*, 1639 (1969) and German Offenlegungsschrift No. 1,953,232, published Apr. 30, 1970, and in British Pat. No. 1,097,533, published Jan. 3, 1968.

More recently, Bagli and Bogri have extended the scope of their processes for preparing 9,15-dioxygenated derivatives of prostanoic acid to include the preparation of 9-oxo-15-hydroxy prostanoic acid derivatives having an alkyl substituent at position 15, U.S. Pat. No. 3,671,570, issued June 20, 1972. These 15-alkyl derivatives possess hypotensive, antihypertensive, bronchospasmolytic and gastric acid secretion inhibiting properties, as well as inhibiting the aggregation of platelets and promoting the disaggregation of aggregated platelets.

Still further improvements in the synthesis of such 9,15-dioxygenated derivatives are described in U.S. Pat. No. 3,773,795, issued Nov. 20, 1973, U.S. patent application Ser. No. 351,381, filed Apr. 16, 1973 and the publication by N. A. Abraham, *Tetrahedron Letters*, 451 (1973).

Other recent syntheses of 9,15-dioxygenated derivatives are reported in Belgian Pat. No. 766,521, published Nov. 3, 1971, P. Crabbé and A. Guzman, *Tetrahedron Letters*, 115 (1972), M. P. L. Caton, et al., *Tetrahedron Letters*, 773 (1972), C. J. Sih, et al., *Tetrahedron Letters*, 2435 (1972), F. S. Alverez, et al., *J. Amer. Chem. Soc.*, 94, 7823 (1972), A. F. Kluge, et al. and *J. Amer. Chem. Soc.*, 94, 9256 (1972).

It is noteworthy that the synthetic 9,15-dioxygenated prostanoic acid derivatives described above possess a number of the biological activities of the natural compounds although they lack the 11-hydroxyl of the latter.

In addition it should be noted that the natural PGE$_1$, PGE$_2$, PGF$_1$$_\alpha$ and PGF$_2$$_\alpha$ do have the disadvantage of being relatively unstable, see T. O. Oesterling, et al., *J. Pharm. Sci.*, 61, 1861 (1972). For example, it is well known that the 11-hydroxy group of PGE$_1$ and PGE$_2$ participates readily in dehydration reactions under both basic and acidic conditions, see S. Bergstrom et al., *J. Biol. Chem.* 238, 3555 (1963), E. J. Corey et al., *J. Amer. Chem. Soc.*, 90, 3245 (1968), J. E. Pike et al., *J. Org. Chem.* 34, 3552 (1969) and "The Prostaglandins, Progress in Research", S. M. M. Karim, Ed., Wiley-Interscience, New York, 1972, p. 10.

As realized by those skilled in the art this inherent disadvantage of the natural compounds must always be taken into account when considering the practical aspects of preparation, formulation or storage of these compounds. In contrast, the compounds of the present invention are free from this disadvantage.

It is the purpose of the present disclosure to describe certain 9,15-dioxygenated prostanoic acid derivatives possessing useful pharmacologic properties coupled with a relatively low order of toxicity. Furthermore, there is disclosed a process for preparing the derivatives which starts from readily available starting materials, avoids noxious agents, is executed facilely and is adaptable to large scale preparation of the derivatives.

For example, the present process utilizes as one of its starting materials a dialkyl 2-(carboalkoxymethyl)malonate (formula 3, see below), which is readily prepared by condensing a dialkyl malonate with the appropriate readily available lower alkyl haloacetic acid. The ready availability of this starting material represents an improvement over our earlier process of U.S. patent application Ser. No. 238,650, filed Mar. 27, 1973 (see also corresponding West German Offenlegungsschrift No. 2,313,686, published Apr. 10, 1973). The earlier process utilizes a substituted malonate derivative which in some cases takes a seven or eight step synthesis to prepare.

Other advantages of the present process are that it yields directly prostaglandin derivatives having the hydroxy group of the cyclopentane ring in the most desirable configuration. In other words the more active epimer with respect to the configuration of the cyclopentane hydroxy group is obtained. Furthermore, this desirable result can be achieved with simple and non-hazardous reagents, for example by reducing the appropriate precursor ketone with sodium borohydride, thereby eliminating the necessity of using noxious or expensive reagents; cf. E. J. Corey, et al., *J. Amer. Chem. Soc.*, 93, 1491 (1971).

Still another advantage of the present process features the preparation of an entirely new class of prostaglandin derivatives in which the acid side chain is unsaturated and the side chain bearing the hydroxy group is fully saturated.

The foregoing advantages render the prostaglandin derivatives of this invention particularly desirable as pharmacologic agents.

SUMMARY OF THE INVENTION

One aspect of this invention is a process for the preparation of the key intermediates, the hydroxylactone 6 and the ketolacetone of formula 7. The process is represented by the following flow diagram:

alkyl cyclopropanedicarboxylate of formula 1 in which $R^1$, $R^2$, $R^4$, $R^5$, $R^6$ and n are as defined herein is condensed with a triester of formula 2 in which $R^3$ is lower alkyl in the presence of a base to give the corresponding cyclopentanonetriester of formula 3. When $R^2$ of the latter compound is a hydroxy protecting radical,

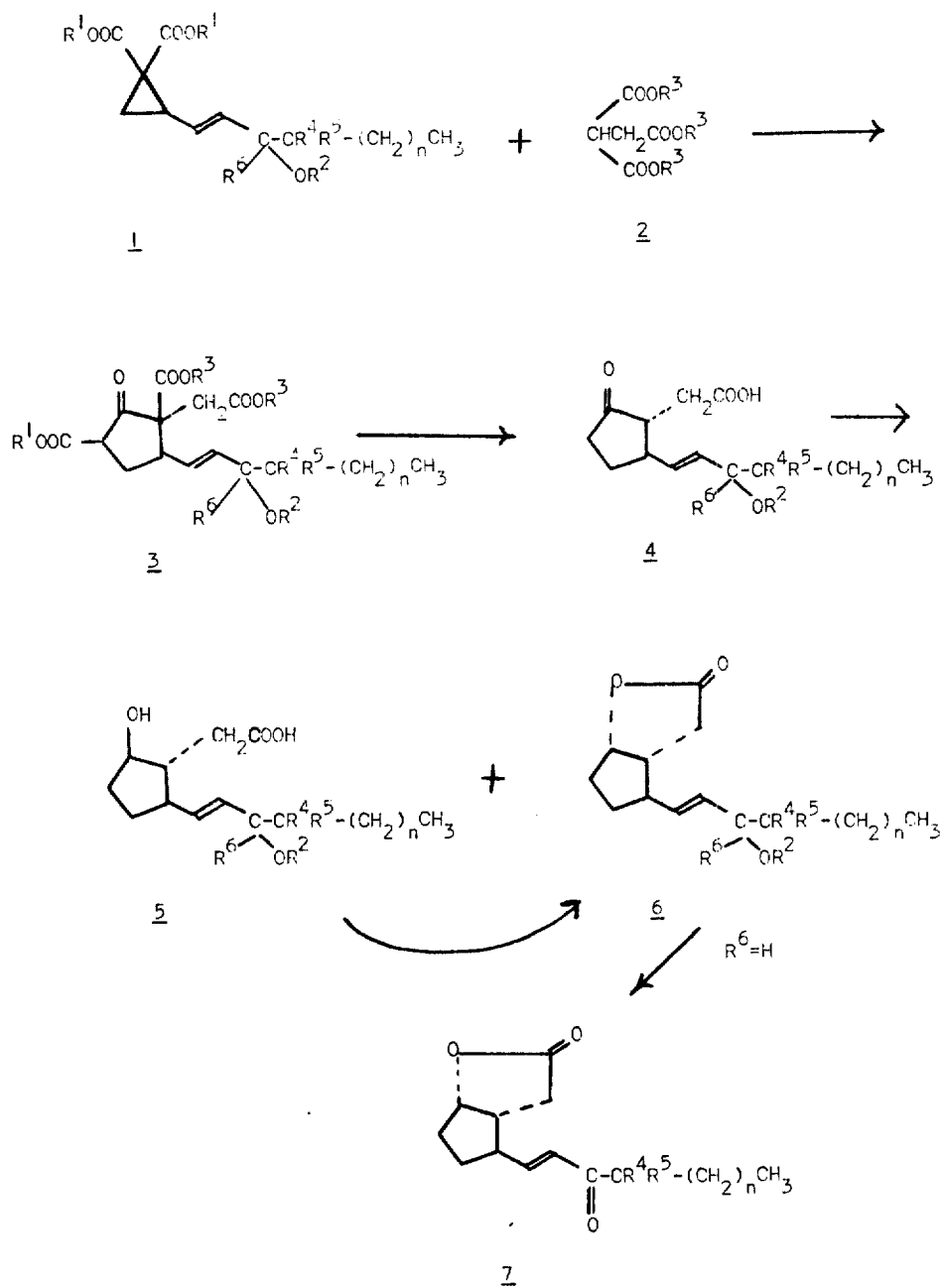

in which $R^1$ and $R^3$ are each lower alkyl, $R^2$ is hydrogen or a hydroxy protecting radical, $R^4$, $R^5$ and $R^6$ each are hydrogen or lower alkyl, and n is an integer from two to five with the provisos that at least one of $R^4$, $R^5$ or $R^6$ is hydrogen and that $R^2$ is hydrogen when $R^6$ is lower alkyl.

With reference to the above flow diagram a lower the radical is removed by treating the cyclopentanonetriester with a deprotecting agent to give the corresponding cyclopentanonetriester of formula 3 in which $R^2$ is hydrogen. The instant compound of formula 3 in which $R^2$ is hydrogen is now subjected to base treatment in the presence of water, followed by acidification of the basic reaction mixture to give the corresponding γ-ketoacid of formula 4. In the case where $R^6$ is hydrogen the latter compound is transformed to its corresponding hydroxy protected derivative (4, $R^2$ = hydroxy protecting radical). The compound of formula 4 in which $R^6$ is hydrogen or lower alkyl is reduced with a complex borohydride to give a mixture of the corresponding acid of formula 5 and the corresponding hydroxylactone 6. Transformation of the acid 5 to the hydroxylactone 6, thereby increasing the yield of the hydroxylactone 6, is effected by subjecting the acid 5, or the mixture of the acid 5 and the hydroxylactone 6, obtained as above, to treatment with methanesulfonyl or p-toluenesulfonyl chloride or bromide in the presence of a suitable proton acceptor. In the case where the hydroxylactone of formula 6 is obtained in the form of its corresponding hydroxy protected derivative (6, $R^2$ = hydroxy protecting group and $R^6$ = H), the protected derivative is converted readily to its corresponding free hydroxy derivative (6, $R^2$ = H) by treatment with a deprotecting agent.

On subjecting the latter free hydroxy derivative of formula 6 in which $R^6$ is hydrogen to oxidation with an agent known to be effective for oxidizing allylic alcohols to α,β-unsaturated ketones, the corresponding desired ketolactone of formula 7 in which $R^4$ and $R^5$ each are hydrogen or lower alkyl and n is an integer from two to five is obtained. One of these ketolactones has been reported previously; i.e., the compound of formula 7 in which $R^4$ and $R^5$ each are hydrogen and $n$ = 3, see E. J. Corey and R. Ravindranathan, *Tetrahedron Letters*, 4755 (1971).

The ketolactone of formula 7 is transformed to prost-5-enoic and prosta-5,13-dienoic acid derivatives and related homologs according to one of the following three methods A, B, or C:

In method A the ketolactone of formula 7 is reduced catalytically to give the corresponding dihydroketolactone of formula 8

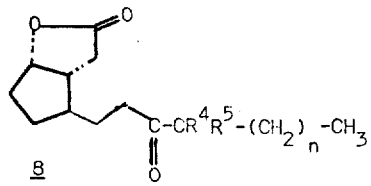

8

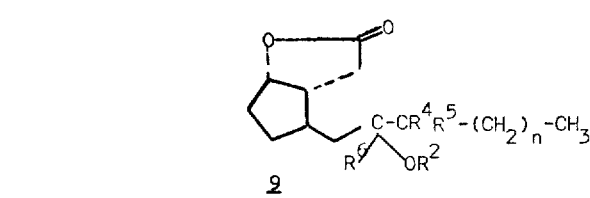

9 in which $R^4$, $R^5$ and n are as defined herein. Subsequent reduction of the latter compound with a metal borohydride yields the corresponding dihydrohydroxylactone of formula 9 in which $R^2$ and $R^6$ are hydrogen and $R^4$, $R^5$ and n are as defined herein. Thereafter, the latter dihydrohydroxylactone of formula 9, or preferably its hydroxy protected derivative, is reduced with a mono- or dialkyl aluminum hydride to give the corresponding hemiacetal of formula 10

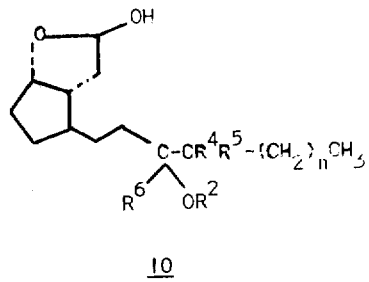

10 in which $R^2$ is hydrogen or a hydroxy protecting group. $R^6$ is hydrogen, and $R^4$, $R^5$ and n are as defined herein. Condensation of the latter compound with a Wittig reagent of the formula

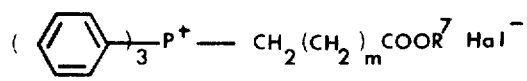

in which Hal is bromine, chlorine or iodine, m is an integer from one to three and $R^7$ is hydrogen or lower alkyl yields the corresponding novel prostaglandin derivative of formula 11

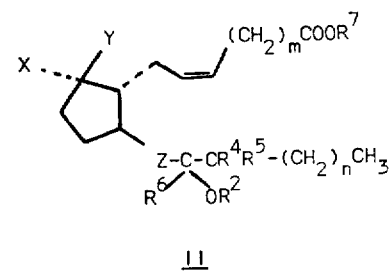

11 in which $R^2$ is hydrogen or a hydroxy protecting group, $R^6$ is hydrogen, X is hydroxy, Y is hydrogen, Z is $CH_2CH_2$ and $R^4$, $R^5$, $R^7$, m and n are as defined herein; and when $R^2$ of the latter compound is a hydroxy protecting group, subsequent reaction of the latter compound with a deprotecting agent for removing the protecting group yields the corresponding compound of formula 11 in which $R^2$ is hydrogen.

In method B the ketolactone of formula 7 in which $R^4$ is hydrogen and $R^5$ and n are as defined herein is reduced catalytically in the same manner as described in the method A and the resulting corresponding dihydroketolactone of formula 8 ($R^4$ = H and $R^5$ = H or lower alkyl) is reacted with substantially one equivalent of a lower alkyl magnesium halide (i.e. a Grignard type reaction) to yield the corresponding dihydrohydroxylactone of formula 9 in which $R^2$ is hydrogen, $R^6$ is lower alkyl, $R^4$ is hydrogen and $R^5$ and n are as defined herein. Subsequent reduction of the latter compound with a mono- or dialkyl aluminum hydride gives the corresponding hemiacetal of formula 10 in which $R^2$ is hydrogen, $R^6$ is lower alkyl and $R^4$ is hydrogen and $R^5$ and n are as defined herein which is condensed in a like manner with the appropriate Wittig reagent as described in the first method to yield the corresponding novel prostaglandin derivative of formula 11 in which $R^2$ and $R^4$ each are hydrogen, $R^6$ is lower alkyl, X is hydroxy, Y is hydrogen, Z is $CH_2CH_2$ and $R^5$, $R^7$, m and n are as defined herein.

In method C the ketolactone of formula 7 in which $R^4$ is hydrogen and $R^5$ and n are as defined herein is reacted with a lower alkyl magnesium halide to produce the corresponding hydroxylactone of formula 12

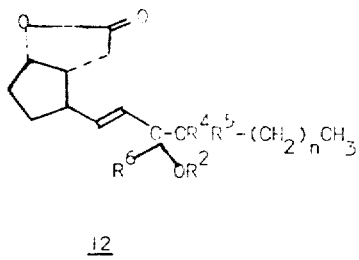

12 in which $R^2$ is hydrogen, $R^4$ is hydrogen, $R^6$ is lower alkyl, and $R^5$ and n are as defined herein. The latter compound is reduced with a monoalkyl or dialkyl aluminum hydride to give the corresponding hemiacetal of formula 13

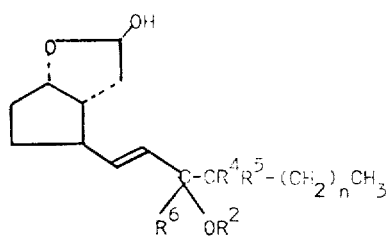

13 in which $R^2$ is hydrogen, $R^4$ is hydrogen, $R^6$ is lower alkyl, and $R^5$ and n are as defined herein. Subsequent condensation of the hemiacetal of formula 13 with the appropriate Wittig reagent as described in the first method gives the prostaglandin derivatives of formula 11 in which $R^2$ and $R^4$ each are hydrogen, $R^6$ is lower alkyl, X is hydroxy, Y is hydrogen, Z is trans CH=CH, and $R^5$, $R^7$, m and n are as defined herein.

These prostaglandin derivatives, prepared by a different process, are part of the subject matter of our U.S. Pat. No. 3,773,795, issued Nov. 20, 1973 and Ser. No. 351,381, filed Apr. 16, 1973.

In another aspect of this invention the hydroxylactone of formula 6 in which $R^2$, $R^4$, $R^5$ and n are as defined in the first instance is utilized to prepare prostaglandin derivatives by one of the following two methods, D or E:

In method D the hydroxylactone of formula 6 in which $R^6$ is hydrogen, preferably in its protected hydroxyl form (i.e., $R^2$ is a hydroxy protecting group), is reduced catalytically to give the corresponding dihydrohydroxylactone of formula 9 in which $R^2$ is hydrogen or a hydroxy protecting group, $R^6$ is hydrogen and $R^4$, $R^5$ and n are as defined in the first instance. Thereafter, the latter dihydrohydroxylactone, preferably in its protected hydroxyl form, is transformed to the corresponding novel prostaglandin derivative of formula 11, through the hemiacetal (10; $R^2$ being hydrogen or a hydroxy protecting group, $R^6$ being hydrogen and $R^4$, $R^5$ and n being as defined in the first instance) by reduction wih a mono- or dialkylaluminum hydride to the corresponding hemiacetal followed by condensation with the appropriate Wittig reagent in the manner descried previously. In this manner the same prostaglandin derivatives are obtained as those obtained by transforming the ketolactone of formula 7 according to the method A described hereinbefore, i.e., the derivatives of formula 11 in which $R^2$ is hydrogen or a hydroxy protecting group, $R^6$ is hydrogen, X is hydroxy, Y is hydrogen, Z is $CH_2CH_2$ and $R^4$, $R^5$, $R^7$, m and n are as defined in the first instance.

In method E for transforming the hydroxylactone of formula 6 in which $R^2$, $R^4$, $R^5$, $R^6$ and n are as defined in the first instance to prostaglandin derivatives, the hydroxylactone of formula 6, preferably in its protected hydroxyl form when $R^6$ is hydrogen, is reduced to its corresponding hemiacetal of formula 13 in which $R^2$, $R^4$, $R^5$, $R^6$ and n are as defined in the first instance by treatment with a monoalkyl or dialkyl aluminum hydride. Thereafter, the latter hemiacetal, preferably in its protected hydroxyl form when $R^2$ is hydrogen, is condensed with a Wittig reagent in the manner described above to yield the corresponding prostaglandin derivatives of formula 11 in which $R^2$ is hydrogen or a hydroxy protecting group and $R^6$ is hydrogen or $R^2$ is hydrogen and $R^6$ is lower alkyl, X is hydroxy, Y is hydrogen, Z is trans CH=CH, and $R^4$, $R^5$, $R^7$, m and n are as defined in the first instance; and when $R^2$ of the latter compound is a hydroxy protecting radical, treating said latter compound with a deprotecting agent for removing the radical to obtain the corresponding compound of formula 11 in which $R^2$ is hydrogen. These latter prostaglandin derivatives, prepared by another process, are part of the subject matter of our copending U.S. application, Ser. No. 351,381, filed Apr. 16, 1973.

Thereafter, if desired, the aforementioned compounds of formula 11 in which $R^2$ is a hydroxy protecting group, $R^4$ is hydrogen or lower alkyl and $R^6$ is hydrogen, or $R^2$ and $R^4$ each are hydrogen and $R^6$ is a lower alkyl; $R^7$ is hydrogen, X is hydroxy, Y is hydrogen and Z is $CH_2CH_2$ or trans CH=CH and $R^5$, m and n are as defined in the first instance, are treated with an agent capable of oxidizing the hydroxy function to its corresponding keto function to obtain the corresponding compound of formula 11 in which X and Y together are oxo, followed, when $R^2$ of the latter compound is a hydroxy protecting group, by reacting the latter compound with a deprotecting agent to obtain the corresponding compound of formula 11 in which $R^2$ is hydrogen.

Furthermore, if desired, the aforementioned compound of formula 11 in which $R^2$ and $R^7$ are hydrogen, X is hydroxy and Y is hydrogen or X and Y together are oxo and Z is $CH_2CH_2$ or CH=CH and $R^4$, $R^5$, $R^6$, m and n are as defined in the first instance, are treated with a lower alkanol containing one to three carbons in the presence of an acid catalyst to obtain its corresponding ester derivative of formula 11 in which $R^7$ is lower alkyl.

DETAILS OF THE INVENTION

The numbering system applied to the compounds of this invention, as used hereinafter, refers to the ω-cyclopentyl(lower)alkanoic acid nucleus.

A feature of this invention is that the process described herein leads to the compounds of formula 11 in which the two side chains are in the trans configuration characteristic for the natural prostaglandins. Also, like the natural prostaglandins a double bond in the acid side chain of the compounds of this invention has the cis configuration and the double bond in the side chain bearing the hydroxy group has the trans configuration.

Notwithstanding the preceding considerations the compounds of this invention having one or more asymmetric carbon atoms can exist in the form of various stereochemical isomers. More specifically, the compounds are produced as a mixture of racemates. These mixtures result from the asymmetric centers, for example the carbon bearing a hydroxyl group, and can be separated into pure racemates at appropriate stages by methods well known in the art, for example, see below. If desired, the racemates can be resolved into enantiomorphs also by known methods. It is to be understood that such racemates and enantiomorphs are included within the scope of this invention.

Furthermore, it is to be understood that the pictorial representations used herein illustrating the compounds of this invention, are to be construed as including such racemates and enantiomorphs. For example, in formula 11 the dotted line joining the acid side chain to the cyclopentane ring and the solid line joining the side chain bearing the hydroxy group are used for the purpose of illustrating the trans relationship of these two side chains and should not be construed as limiting the compounds to one enantiomorph but rather as including all possible enantiomorphs having this trans relationship.

Also included within this invention are the pharmaceutically acceptable salts of the acids of formula 11 in which $R^7$ is hydrogen. The latter compounds are transformed in excellent yield into the corresponding pharmaceutically acceptable salts by neutralization of said latter compounds with the appropriate inorganic or organic base. The relative stability of the acid faciitates this transformation. The salts possess the same activities as the parent acid compounds when administered to animals and may be utilized in the same manner. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines: lower mono-, di- and trialkylamines, the alkyl radicals of which contain up to 3 carbon atoms, such as methylamine, dimethylamine, trimethylamine, ethylamine, di- and triethylamine, methylethylamine, and the like; mono-, di-and trialkanolamines, the alkanol radicals of which contain up to 3 carbon atoms, such as mono-, di- and triethanolamine; alkylene-diamines which contain up to 6 carbon atoms, such as hexamethylenediamine; cyclic saturated or unsaturated bases containing up to 6 carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyl-triethanol and trimethyl-monoethanol) and cyclic ammonium salts, for example the N-methylpyridinium, N-methyl-N-(2-hydroxyethyl)-pyrrolidinium, N,N-dimethylmorpholinium, N-methyl-N-(2-hydroxyethyl)-morpholinium, N,N-dimethylpiperidinium and N-methyl-N-(2-hydroxyethyl)-piperidinium salts, which are characterized by an especially good water-solubility. In principle, however, there can be used all ammonium salts which are physiologically compatible.

The transformations to the salts can be carried out by a variety of methods known in the art. For example, in the case of the inorganic salts, it is preferred to dissolve the selected acid in water containing at least an equivalent amount of a hydroxide, carbonate, or bicarbonate corresponding to the inorganic salt desired. Advantageously, the reaction is performed in an inert organic solvent, for example, methanol, ethanol, dioxane, and the like. For example, such use of sodium hydroxide, sodium carbonate or sodium bicarbonate gives a solution of the sodium salt. Evaporation of the water or addition of a water-miscible solvent of moderate polarity, for example, a lower alkanol or a lower alkanone gives the solid inorganic salt if that form is desired.

To produce an amine salt, the selected acid is dissolved in a suitable solvent of either moderate or lower polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or diethyl ether or by evaporation. If the amine is relatively volatile, any excess can easily be removed by evaporation. It is preferred to use equivalent amounts of the less volatile amines.

Salts wherein the cation is quaternary ammonium are produced by mixing the selected acid with an equivalent amount of the corresponding quaternary ammonium hydroxide in water solution, followed by evaporation of the water.

The term "lower alkyl" as used herein contemplates straight chain alkyl groups containing from one to three carbon atoms and includes methyl, ethyl and propyl.

The term "complex borohydride" as used herein contemplates the metal borohydrides, including sodium borohydride, potassium borohydride, lithium borohydride, zinc borohydride and the like, and metal trihydrocarbylborohydrides including lithium 9-alkyl-9-borabicyclo[3,3,1]-nonylhydride, in which the alkyl contains one to seven carbon atoms, preferably lithium 9-tert-butyl-9-borabicyclo-[3,3,1]nonylhydride, prepared according to the procedure described in German Offenlegungsschrift No. 2,207,987, published Aug. 31, 1972, lithium diisopinocamphenyl-tert-butylborohydride and lithium 2-thexyl-4,8-dimethyl-2-borobicyclo[3,3,1]nonylhydride, described by E. J. Corey et al., *J. Amer. Chem. Soc.*, 93, 1491 (1971), lithium perhydro9b-borophenalylhydride, described by H. C. Brown and W. C. Dickason, *J. Amer. Chem. Soc.*, 92, 709 (1970) and the like.

The compounds of formula 11 possess interesting pharmacological properties when tested in standard pharmacological tests. In particular, they have been found to possess hypotensive, antihypertensive, bronchospasmolytic, gastric acid secretion inhibiting, abortifacient and estrus synchronizing and ovulation regulating properties, which make them useful in the treatment of conditions associated with high blood pressure, in the treatment of asthmatic conditions, in the treatment of pathological conditions associated with excessive secretion of gastric acid such as, for example, peptic ulcer, in population control, and in animal husbandry. In addition, the compounds of this invention inhibit the aggregation of platelets and promote the disaggregation of aggregated platelets, and are useful as agents for the prevention and treatment of thrombosis.

More particularly, these compounds, when tested in a modification of the tests for determining hypotensive activities described in "Screening Methods in Pharmacology", Academic Press, New York and London 1965, page 146, using the cat in urethane-chloralose anaesthesia as the test animal and measuring mean arterial blood pressure before and after intravenous administration of the compounds, have exhibited utility as hypotensive agents. When tested in the renal hypertensive rat, prepared by the method of A. Grollman described in *Proc. Soc. Exp. Biol. Med.*, 7, 102 (1954), and measuring blood pressure by the method described by H. Kersten, *J. Lab. Clin. Med.*, 32, 1090 (1947), they have exhibited utility as antihypertensive agents.

Moreover, the compounds of this invention, when tested in a modification of the test method described by A. K. Armitage, et al., *Brit. J. Pharmacol.*, 16, 59 (1961), have been found to alleviate bronchospasms, and are useful as bronchospasmolytic agents.

Furthermore, the compounds of this invention, when administered to rats in the test method described by H. Shay, et al., *Gastroenterol.*, 26, 906 (1954), have been found to inhibit the secretion of gastric acid, and are useful as agents inhibiting the secretion of gastric acid.

In addition, the compounds of this invention, when tested in a modification of the test method described by G. V. R. Born, *Nature*, 194, 927 (1962), using the aggregometer manufactured by Bryston Manufacturing Limited, Rexdale, Ontario, Canada, have been shown to inhibit the aggregation of platelets and to promote the disaggregation of aggregated platelets, and are useful as agents for the prevention and treatment of thrombosis.

When the compounds of this invention are employed as hypotensive or anti-hypertensive agents, as agents inhibiting gastric acid secretion in warm-blooded animals, for example, in cats or rats, as agents for the prevention or treatment of thrombosis, or as bronchospasmolytic agents, alone or in combination with pharmacologically acceptable carriers, their proportions are determined by their solubilities, by the chosen route of administration, and by standard biological practice. The compounds of this invention may be administered orally in solid form containing such excipients as starch, lactose, sucrose, certain types of clay, and flavouring and coating agents. However, they are preferably administered parenterally in the form of sterile solutions thereof which may also contain other solutes, for example, sufficient sodium chloride or glucose to make the solution isotonic. For use as bronchospasmolytic agents, the compounds of this invention are preferably administered as aerosols.

The dosage of the present hypotensive, antihypertensive, gastric acid secretion inhibiting, or bronchospasmolytic agents, or agents for the prevention and treatment of thrombosis will vary with the forms of administration and the particular hosts under treatment. Generally, treatments are initiated with small dosages substantially less than the optimum doses of the compounds. Thereafter, the dosages are increased by small increments until the optimum effects under the circumstances are reached. In general, the compounds of this invention are most desirably administered at a concentration level that will generally afford effective results without causing any harmful or deleterious side effects and preferably at a level that is in a range of from about 0.1 mg to about 10.0 mg per kilo, although as aforementioned variations will occur. However, a dosage level that is in the range of from about 0.5 mg to about 5 mg per kilo is most desirably employed in order to achieve effective results. When administering the compounds of this invention as aerosols the liquid to be nebulized, for example, water, ethyl alcohol, dichlorotetrafluoroethane and dischlorodifluoromethane, contains preferably from 0.005–0.05 per cent of the acid, or a non-toxic alkali metal, ammonium or amine salt thereof, or ester of formula 11.

Furthermore, when the compounds of this invention are tested by the method of A. P. Labhsetwar, *Nature*, 230, 528 (1971) whereby the compound is given subcutaneously on a daily basis to mated hamsters on days 4, 5 and 6 of pregnancy, thereafter the animals being sacrificed on day 7 of pregnancy and the number of abortions counted, the compounds are shown to have abortifacient properties.

For example, complete abortion resulted in all animals when the following compounds of formula 11 were tested according to this method at doses noted below: trans,cis-7-[2α-hydroxy-5-(3-hydroxy-3-methyl-1-octenyl)cyclopentyl]-5-heptenoic acid (Example 175), 0.5 mg/kg/day, cis-7-[2α-hydroxyl-5-(3-hydroxyoctyl)cyclopentyl]-5-heptenoic acid (Example 175), 2.5 mg/kg/day, and cis-7-[2α-hydroxy-5-(3-hdyroxy-3-methyloctyl)cyclopentyl]-5-heptenoic acid (Example 175), 5.0 mg/kg/day.

The potency of the above unsaturated compounds is especially noteworthy in light of the fact that the completely saturated 15methyl analog, 2-(3-hydroxy-3-methyloctyl-5-oxocyclopentancheptanoic acid, described in U.S. Pat. No. 3,671,570, cited above, does not cause complete abortion in the above test at doses less than 30 mg/kg/day.

Furthermore, the compounds of this invention are useful for inducing labor in pregnant animals at or near term. When the compounds of this invention are employed as agents for abortion or for inducing labor, the compounds are infused intravenously at a dose of 0.01 to 100 mg/kg per minute until the desired effect is obtained.

Still furthermore, the compounds of formula 11 are useful for the synchronization of estrus and the regulation of ovulation in animals.

It is often desirable to synchronize estrus in domestic animals, for example, horses, cattle, sheep, swine or dogs, in order to be able to perform artificial insemination or mating with a male of the desired genetic quality under optimum conditions. In the past, this has been done by administering to the animals an ovulation-inhibiting agent, withdrawing administration of said agent shortly before the date chosen for mating or artificial insemination, and relying either upon the natural production of LH and FSH to induce ovulation and to produce estrus or by administering gonadotrophins. However, this procedure was not entirely satisfactory because ovulation at a predetermined time occured only in a certain proportion of the animals when gonadotrophins were not used. On the other hand, the high cost of gonadotrophins and side effects encountered in their administration made this method impractical. It is now possible to obtain substantially complete synchronization of ovulation and of estrus, by treating the animals in a given group with the compound of formula 11 before the predetermined period of time for mating or artificial insemination, so as to obtain ovulation and estrus within that time interval. The delay in the onset of ovulation and estrus following administration of the compound of this invention varies with the species of animal. For example, in rodents such as rats or hamsters ovulation takes place within 18 hours following administration of the compound and in the horse ovulation usually takes place within one week after the compound is given.

More specifically, synchronization of estrus and regulation of ovulation in the horse is achieved by giving the compound of formula 11 either randomly to a group of horses during the life of the corpus luteum (usually day 5 to day 16 of the cycle) or two to three days prior to the expected onset of estrus. The compound for example, trans, cis-7-[2α-hydroxy-5-(3-hydroxy-3-methyl-1-octenyl)cyclopentyl]-5-heptenoic acid, is given by intrauterine infusion, subcutaneously or intramuscularly in sterile solutions. A dosage which is in the range of from about 1 to 100 mg/1000 lb., preferably 5 to 25 mg/1000 lb is employed and is administered as a single dose or spread over a period of 72 hours. Practically speaking it is preferable to give one-half the total dose on two consecutive days for the latter form of administration. For example, in a group of horses receiving this medication on the second and third day before expected estrus, estrus follows within 24 to 48 hours which in turn is followed by ovulation occuring in the majority of animals, from the fourth to the sixth day thereafter as determined by rectal palpation of the ovaries.

In a control group receiving no medication the occurance of ovulation was spread rather unevenly over the third to eighth day after the onset of estrus.

PROCESS

The starting materials of formula 1 are described in U.S. Pat. No. 3,773,795 and the U.S. patent application Ser. No. 351,381, cited above; see also West German Offenlegungsschrift No. 2,313,686, published Apr. 10, 1973 and the publication by N. A. Abraham, cited above.

Briefly the starting materials are prepared readily by treating an aldehyde of formula 14 herein; followed by reduction of the latter compound with a metal borohydride, preferably sodium borohydride, to obtain the corresponding starting material of formula 1 in which $R^2$ is hydrogen, which in turn is readily transformed to its corresponding hydroxy protected derivative. The starting material of formula 1 in which $R^6$ is lower alkyl is obtained by reacting the ketodicarboxylic acid of formula 15 with substantially one molar equivalent of a lower alkyl magnesium halide in the manner described herein.

The aldehyde of formula 14 in which $R^1$ is ethyl, required for the preceding preparation, has been described by D. T. Warner, *J. Org. Chem.*, 24, 1536 (1959). By following the process described therein for the preparation of that aldehyde and using the appropriate di(lower)alkylbromomalonate, the aldehydes of formula 14 in which $R^1$ is a lower alkyl other than ethyl are obtained.

The requisite Wittig reagents are prepared by the method of E. J. Corey and G. T. Kwiatkowsky, *J. Amer. Chem. Soc.*, 88, 5654 (1966) using the appropriate lower alkyl alkanoate and di(lower()alkyl α-lithiomethanephosphonate.

The triester of formula 3, the other starting material of this process, is readily prepared by condensing a di(lower)alkyl malonate with a lower alkyl bromoacetic acid ester in the presence of a base. For example, the preparation of the triester of formula 2 in which $R^3$ is ethyl has been described by A. Horeau, *Bull. Soc. Chim. Fr.*, 1959 (1943) and by T. R. Kasturi, Indian Inst. Sci., *Golden Jubilee Research* Vol., 1909–59, 40 (Publ. 1959); see *Chem. Abstr.*, 55, 23371 *h* (1961).

The preferred hydroxy protecting groups for use in the process of this invention are tetrahydropyran-2-yl (THP), trimethylsilyl (TMS), dimethylisopropylsilyl (DMIS), dimethyl-tert-butylsilyl and tert-butyl. The transformation of the free hydroxy derivative to the hydroxy protected derivative is effected by treating the hydroxy derivative with a reagent known to be effective for converting a hydroxy group of a known compound to a protected hydroxy group. Such reagents include an excess of dihydropyran and an acid catalyst for example, p-toluenesulfonic acid, hydrogen chloride or sulfuric acid for the THP group, trimethylchlorosilane with hexamethyldisilazane for the TMS group, dimethylisopropylchlorosilane and diisopropyltetramethyldisilazane for the DMIS group, dimethyl-tert-butylchlorosilane and imidazole for the dimethyl-tert-butylsilyl group or isobutylene for the tert-butyl group.

For removal of the hydroxy protecting groups various agents known to be effective for this purpose are available. These agents are called deprotecting agents. For

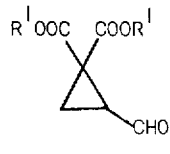

14

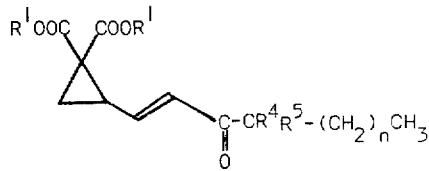

15 in which $R^1$ is lower alkyl with a Wittig reagent of formula $(AlKO)_2POCH_2COCR^4R^5—(CH_2)_nCH_3$ in which Alk is lower alkyl and $R^4$, $R^5$ and n are as defined herein to obtain the corresponding ketodicarboxylic acid of formula 15 in which $R^1$, $R^4$, $R^5$ and n are as defined example, the THP group is removed by treating the derivative having a THP group as the hydroxy protecting group with an acid, for example, hydrochloric acid, aqueous acetic acid or preferably p-toluenesulfonic acid, in an inert solvent in the presence of water, preferably methanol-water (9:1). The TMS radical is removed by treatment with an excess of water-methanol (10:1) for 24 hours or with tetrahydrofuran-acetic acid at room temperature for one to two hours. Likewise, the DMIS and dimethyltert-butylsilyl group are removed by the same conditions used for the removal of the TMS radical.

In practising the process of this invention the starting material of formula 1, preferable in the form of its THP derivative, and the triester of formula 2, preferably, the triethyl ester, are subjected to a base catalyzed condensation to give the corresponding cyclopentanonetriester of formula 3. This condensation is performed in the presence of a suitable base, preferably an alkali metal alkoxide, for example, sodium methoxide. Other suitable bases include sodium ethoxide, potassium tert-butoxide, and sodium hydride. More specifically, this condensation is conveniently effected by heating a mixture of about equimolar amounts of the compound of formula 1 and the triester 2 at 80° to 150°C, preferably 100° to 140°C, for 30 minutes to 6 hours, preferably 1 to 3 hours. The reaction mixture is then cooled, neutralized with an acid, for example, acetic acid, and extracted with a water-immiscible solvent, for example, diethyl ether. Evaporation of the extract and purification of the residue by chromatography on silica gel yields the cyclopentanonetriester of formula 3.

Thereafter, in the case where the hydroxy group has been protected by a suitable protecting group, said group is now removed by a deprotecting agent. The compound of formula 3 in its free hydroxy form is now treated with an alkali metal hydroxide in the presence of water to give the corresponding γ-ketoacid of formula 4 in which $R^2$, $R^4$, $R^5$, $R^6$ and $n$ are as defined in the first instance. Preferably this reaction is done by heating a mixture of the cyclopentanonetriester with an alkali metal hydroxide, preferably sodium hydroxide or potassium hydroxide, in the presence of water at reflux temperature of the mixture for a period of 15 minutes to 6 hours, preferably about 1 to 3 hours. Neutralization of the reaction mixture with acid, for example, 2N HCl, extraction with a water-immiscible solvent, for example, diethyl ether, and subsequent work up of the extract yields the desired γ-ketoacid of formula 4 as a mixture of stereoisomers, i.e., a mixture of trans and cis isomers with respect to the side chains of the cyclopentanone ring. The trans isomers, as shown in formula 4, is the preponderate isomer of the mixture.

Thereafter, the latter compound is converted to its corresponding hydroxy protected derivative, which is treated with a complex borohydride to give a mixture of the corresponding acid 5 and hydroxylactone 6.

This reduction is carried out preferably by treating the γ-ketoacid with sodium borohydride in an inert solvent, for example, methanol, ethanol or tetrahydrofuran at −20° to 30°C from 30 minutes to 2 hours. It is desirable to effect this reduction in the presence of about one equivalent of a base, for example, sodium methoxide, or potassium t-butoxide, so that effectively the reduction is performed on the salt of the γ-ketoacid, for example, the sodium or potassium salt, and complex-formation between the acid and the reducing agent, and hence the need for an excess of the latter, is eliminated.

The reduction mixture of compounds 5 and 6 may be separated by conventional techniques, such as extraction or chromatography. However, it has been found practical to treat the mixture according to a procedure for converting the acid 5 to the hydroxylactone 6. The procedure for this latter conversion involves reacting the acid 5 or the mixture of compound 5 and 6 with methanesulfonyl or p-toluenesulfonyl chloride or bromide, in the presence of a proton acceptor, preferably trimethylamine, N-methylmorpholine or pyridine. The reaction is conveniently performed in an inert organic solvent, for example, methylene chloride or tetrahydrofuran. A reaction time of 30 to 180 minutes and a reaction temperature of −30° to 20°C have been found to be practical and effective for this conversion. Under these conditions the preceding conversion apparently involves the transformation of the ring hydroxyl to a mesylate or p-toluenesulfonate, as the case may be, followed by a $S_n2$ displacement of the latter by the carboxyl to give the desired hydroxylactone. Thereafter, if desired, the hydroxylactone of formula 6 in which $R^2$ is a hydroxy protecting group is reacted with a deprotecting agent to give the corresponding hydroxylactone of formula 6 in which $R^2$ is hydrogen.

From the latter key intermediate of formula 6, the key intermediate of formula 7 is obtained. More precisely, the compound of formula 6 in which $R^2$ and $R^6$ are both hydrogen (i.e., a compound of formula 6 in which the side chain alcohol is a secondary alcohol) is oxidized with an agent known to be effective for oxidizing allylic alcohols to α,β-unsaturated ketones. Suitable agents for this purpose include manganese dioxide, selenium dioxide, chloranil and 2,3-dichloro-5,6-dicyano-1,4-benzoquinone. Manganese dioxide is a preferred reagent for this purpose. Treatment of the compound of formula 6 with manganese dioxide at 20° to 70°C for about 1 to 3 hours in an inert organic solvent, for example, chloroform, benzene or carbon tetrachloride, readily gives the desired ketolactone intermediate.

As noted above the key intermediates of formula 6 and 7 are used subsequently to prepare the prostaglandin derivatives of formula 11. Also as noted hereinbefore these subsequent transformations involve some or all of the following types of reaction: catalytic reduction, reduction with a monoalkyl or dialkyl aluminum hydride, treatment with a Wittig reagent, treatment with a lower alkyl magnesium halide and reduction with a metal borohydride. Convenient and effective conditions for effecting these reactions are generalized in the following manner.

The catalytic reduction is accomplished by treating the compound to be hydrogenated with hydrogen in the presence of a hydrogenation catalyst in a nonreactive solvent medium. Suitable catalysts for this purpose include palladium or platinum on a suitable inert carrier or Raney nickel in dioxane. The latter catalyst is preferred for catalytic reduction of the hydroxylactone of formula 6. Suitable nonreactive solvents include ethyl acetate and ethanol.

The reduction with a monoalkyl or dialkyl aluminum hydride is accomplished by subjecting the compound to be reduced to the action of the aluminum hydride reducing agent, for example, ethyl aluminum hydride, isopropyl aluminum hydride or preferably diisolbutyl aluminum hydride, in an inert organic solvent, for example, benzene, ether, hexane or toluene. Although the reaction can be practised over a wide range of temperatures from about −80°C to the reflux temperature of the solvent, preferred temperatures are from −75° to 0°C. Also the reaction is preferably carried out in an atmosphere of an inert gas, for example, nitrogen or argon. Under these conditions this reduction is usually completed within 0.25 to 5 hours.

The Wittig reaction on the hemiacetals of this invention involves the use of a triphenylphosphonium halide of formula

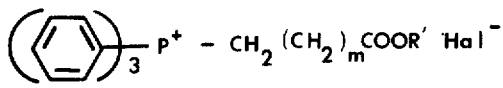

in which $R^7$ is hydrogen or lower alkyl, m is an interger from one to three, and Hal is bromine, chlorine or iodine. The preferred triphenylphosphonium halide is the triphenylphosphonium bromide, i.e. Hal is bromine. The latter reagent is prepared readily by treating the appropriate ω-bromoacid or ω-bromoester of formula $Br-CH_2-(CH_2)_mCOOR^7$ in which m and $R^7$ are as defined hereinbefore with triphenylphosphine in an inert solvent, for example, benzene, or acetonitrile, at 20° to 100°C for 12 to 24 hours and collecting the precipitate. Similarly the corresponding triphenylphosphonium chloride or iodide salts are prepared from appropriate haloacids or haloesters.

The Wittig reaction is carried out by treating the appropriate hemiacetal with about two to ten molar equivalents of the above triphenylphosphonium halide in the presence of four to 20 molar equivalents of a base. For a detailed discussion of the Wittig reaction, see A. Maercker in *Organic Reactions*, Vol. 14, A. C. Cope, et al, Eds. John Wiley and Sons, Inc. New York, 1965, page 3. More particularly, the triphenylphosphonium halide is treated with an excess of a hydrogen halide-binding base, for example, sodium hydride in an inert organic solvent, for example, dimethoxyethane or dimethylformamide, or preferably sodium methylsulfinyl carbanide, prepared from sodium hydride and dimethylsulfoxide [see R. Greenwald, et al., *J. Org. Chem.*, 28, 1128 (1963)]. In this manner the corresponding ylide of the triphenylphosphonium halide is obtained. Subsequent reaction of ylide with the appropriate hemiacetal readily gives the corresponding compound of formula 11. The preparation of the ylide is accomplished readily at 20° to 100°C at 10 to 60 minutes, preferably at 20° to 40°C for about 1 to 2 hours when using sodium hydride is used as the hydrogen halide-binding base, and at 60 to 90°C for about 1 to 2 hours when sodio methylsulfinyl carbanide is used at the base. Thereafter the solution of the resulting ylide is reacted with the appropriate hemiacetal at 20° to 60°C, conveniently room temperature, for a period of time of from 2 to 24 hours. Preferably the reaction is performed in nitrogen atmosphere.

The treatment with a lower alkyl magnesium halide, for example, methyl magnesium bromide, ethyl magnesium chloride, propyl magnesium iodide and the like, is accomplished according to the conditions of the Grignard reaction. Convenient and practical conditions for this addition include ether or tetrahydrofuran as the solvent for the reaction and a reaction temperature of from −80° to 25°C, preferably −10° to 10°C.

The aforementioned treatment of the compounds of formula 11 with an agent capable of oxidizing a hydroxy function to its corresponding keto function is effectively and conveniently accomplished by treating the appropriate compound of formula 11 in which X is hydroxy and Y is hydrogen with one of the agents chromium trioxide-pyridine complex or chromium trioxide-sulfuric acid in acetone, with the latter being preferred.

Finally, reductions with metal borohydride, preferably sodium borohydride, are conveniently performed in a lower alkanol solvent, preferably methanol or ethanol, at 0° to 40°C for 5 to 60 minutes.

The following examples illustrate further this invention. In the examples the temperatures are noted in the Centigrade scale.

EXAMPLE 1

Dimethyl 3,3-dimethyl-2-oxoheptyl phosphonate [$(AlkO)_2POCH_2COCR^4R^5-(CH_2)_nCH_3$ in which Alk is $CH_3$, $R^4$ and $R^5 = CH_3$ and $n = 3$]

The title compound is prepared by treating 2,2-dimethylhexanoic acid methyl ester, S. M. McElvain, et al., *J. Amer. Chem. Soc.*, 75, 3987 (1953), with dimethyl methyl phosphonate according to the procedure of E. J. Corey and G. T. Kwiatkowski, *J. Amer. Chem. Soc.*, 88, 5654 (1966). An exemplification of this procedure is as follows:

Dimethyl methylphosphonate (14.88 g) is dissolved in dry tetrahydrofuran (THF, 34 ml) under a nitrogen atmosphere. The solution is cooled to −78°. Butyllithium (7.68 g, 52 ml of 2.3 molar solution, 3 equiv.) is added very slowly during 1 hour. The mixture is stirred at −78° for 15 minutes. A solution of 2,2-dimethylhexanoic acid methyl ester (6.32 g) in dry THF (16 ml) is added to the cold solution over a period of 1 hour. The mixture is stirred for 30 minutes and then allowed to arm up to room temperature. The reaction mixture is diluted with ether. Dilute (10%) hydrochloric acid (30 ml) is added and the reaction mixture shaken well. The organic phase is separated and washed several times with water, dried (MgSO₄) and the solvent removed. The residue is distilled under reduced pressure to give the title compound, b.p. 110° to 120°10.1mm, $v_{max}^{film}$ 1700, 1250, 1020 cm⁻¹.

Similarly other Wittig reagents of the formula ($AlkO)_2POCH_2COCR^4 R^5-(CH_2)_nCH_3$ in which Alk is an alkyl containing one to three carbon atoms, $R^4$ and $R^5$ are hydrogen or lower alkyl and n is an integer from two to five are prepared by using the appropriate lower alkyl alkanoate and di(lower)alkyl methanephosphonate. For instance, treatment of 2,2-dipropylpentanoic acid methyl ester with dimethyl methylphosphonate gives 2-oxo-3,3-dipropylhexyl phosphonate and treatment of 2,2-diethyloctanoic acid ethyl ester with diethyl methylphosphonate gives 2-oxo-3,3-diethylnonyl phosphonate.

EXAMPLE 2

Dimethyl 2-formylcyclopropane-1,1-dicarboxylate (14; $R^1 = CH_3$)

By following the procedure of D. T. Warner, cited above, used for preparing diethyl 2-formylcyclopropane-1,1-dicarboxylate from acrolein but using equivalent amounts of dimethylbromomalonate and methanol instead of diethylbromomalonate and ethanol, respectively, the title compound, nmr (CDCl₃) δ 1.98 (m, 2H), 2.80 (m, 1H), 3.79 (s, 6H), 8.82 (d, J = 4 cps, 1H), is obtained.

Likewise the use of dipropylbromomalonate and propanol gives dipropyl 2-formylcyclopropane-1,1-dicarboxylate.

EXAMPLE 3

Diethyl trans-2-(4,4-dimethyl-3-oxo-1-octenyl)cyclopropane-1,1-dicarboxylate (15;$R^4$ and $R^5 = CH_3$, $n = 3$ $R^1 = C_2H_5$)

To a suspension of 50% sodium hydride (0.46 g, washed with hexane) in dimethylformamide (DMF) is added a solution of dimethyl 3,3-dimethyl-2-oxoheptyl phosphonate (2.75 g), described in Example 1, in DMF (15 ml) over a period of 30 min. The mixture is stirred and cooled in ice water during the addition and for an additional period of 45 min. A solution of diethyl 2-formylcyclopropane-1,1-dicarboxylate (2.14 g) in DMF (15 ml) is added over 20 min. The reaction mixture is heated at 55° to 60° and stirred for 45 min. The mixture is now cooled in an ice bath and acetic acid is added to render the mixture substantially neutral. The reaction mixture is poured into water (4 × the volume) and the resulting oily precipitate extracted with ether. The extract is washed with water, dried ($Na_2SO_4$) and concentrated. The residue is dissolved in ethyl acetate-benzene (1:9) and the solution poured through a column of silica gel (148 g). The eluate is concentrated to yield the title compound, $\nu_{max}^{film}$ 1725, 1680, 1620 cm$^{-1}$, nmr (CDCl$_3$) δ 0.88 (t, 3H), 4.27 (4H), 6.5, 6.68 and 7.39 (m, 2H), $\lambda_{max}^{EtOH}$ 242 nm (ε = 7500).

In the same manner but replacing diethyl 2-formylcyclopropane-1,1-dicarboxylate with dimethyl 2-formylcyclopropane-1,1-dicarboxylate, dimethyl trans-(4,4-dimethyl-3-oxo-1-octenyl)cyclopropane-1,1-dicarboxylate,$\nu_{max}^{film}$ 1728, 1682 cm$^{-1}$, is obtained.

In the same manner but replacing dimethyl 3,3-dimethyl-2-oxoheptyl phosphonate with an equivalent amount of dimethyl 3-methyl-2-oxoheptyl phosphonate, b.p. 112° to 115°/0.2 mm, prepared from 2-methylhexanoic acid methyl ester or the 2-methylhexanoic acid chloride according to the procedure of Example 1, diethyl trans-2-(4-methyl-3-oxo-1-octenyl)cyclopropane-1,1-dicarboxylate, $\nu_{max}^{film}$ 1725, 1680, 1665, 1620 cm$^{-1}$, nmr (CDCl$_3$) δ 4.19 (q, J = 7, 4H), 6.32 (d, J = 5, 2H), is obtained.

In the same manner but replacing dimethyl 3,3-dimethyl-2-oxoheptyl phosphonate with an equivalent amount of dimethyl-2-oxoheptyl phosphonate, described by E. J. Corey, et al., J. Amer. Chem. Soc., 90, 3247 (1968), diethyl trans-2-(3-oxo-1-octenyl)cyclopropane-1,1-dicarboxylate, b.p. 153° to 154°/0.7 mm, is obtained.

In the same manner but replacing dimethyl 3,3-dimethyl-2-oxoheptylphosphonate with an equivalent amount of dimethyl 3-ethyl-2-oxohexyl phosphonate, dimethyl 3-propyl-2-oxooctyl phosphonate, or dimethyl 3-ethyl-2-oxononyl phosphonate, dimethyl trans-2-(4-ethyl-3-oxo-1-heptenyl)cyclopropane-1,1-dicarboxylate, dimethyl trans-2-(3-oxo-4-propyl-1-nonenyl)cyclopropane-1,1-dicarboxylate and dimethyl trans-2-(4-ethyl-3-oxo-1-decenyl)cyclopropane-1,1-dicarboxylate are obtained, respectively.

By following the procedure of Example 3 and utilizing the appropriate Wittig reagent and the aldehyde of formula 14 then other compounds of formula 15 are obtained. Examples of such compounds of formula 15 are listed in Table I together with the appropriate Wittig reagent and aldehyde of formula 14 utilized for their preparation.

TABLE I

| EX. | Wittig Reagent (AlkO$_2$)POCH$_2$COCR$^4$R$^5$—(CH$_2$)$_n$CH$_3$ | | | | ALDEHYDE 14 R$^1$ | Product: (Prefix Listed below)-cyclopropane 1,1-dicarboxylate |
|---|---|---|---|---|---|---|
| | Alk | R$^4$ | R$^5$ | n | | |
| 4 | CH$_3$ | H | H | 2 | CH$_3$ | dimetyl trans-2-)3-oxo-1-heptenyl) |
| 5 | CH$_3$ | H | H | 4 | C$_2$H$_5$ | diethyl trans-2-(3-oxo-1-nonenyl) |
| 6 | CH$_3$ | H | H | 5 | CH$_3$ | dimethyl trans-2-(3-oxo-1-decenyl) |
| 7 | CH$_3$ | CH$_3$ | H | 2 | C$_2$H$_5$ | diethyl trans-2-(4-methyl-3-oxo-1-heptenyl) |
| 8 | CH$_3$ | CH$_3$ | H | 4 | CH$_3$ | dimethyl trans-2-(4-methyl-3-oxo-1-nonenyl) |
| 9 | CH$_3$ | C$_2$H$_5$ | H | 3 | C$_2$H$_5$ | diethyl trans-2-(4-ethyl-3-oxo-1-octenyl) |
| 10 | CH$_3$ | C$_2$H$_5$ | H | 5 | CH$_3$ | dimethyl trans-2-(4-methyl-3-oxo-1-decenyl) |
| 11 | CH$_3$ | n-C$_3$H$_7$ | H | 2 | C$_2$H$_5$ | diethyl trans-2-(3-oxo-4-propyl-1-heptenyl) |
| 12 | CH$_3$ | n-C$_3$H$_7$ | H | 4 | CH$_3$ | dimethyl trans-2-(3-oxo-4-ethyl-1-nonenyl) |
| 13 | C$_2$H$_5$ | CH$_3$ | CH$_3$ | 5 | n-C$_3$H$_7$ | dipropyl trans-2-(4,4-dimethyl-3-oxo-1-decenyl) |
| 14 | C$_2$H$_5$ | C$_2$H$_5$ | CH$_3$ | 5 | n-C$_3$H$_7$ | dipropyl trans-2-(4-ethyl-4-methyl-3-oxo-1-decenyl) |
| 15 | C$_2$H$_5$ | n-C$_3$H$_7$ | CH$_3$ | 2 | CH$_3$ | dimethyl trans-2-(4-methyl-3-oxo-4-propyl-1-heptenyl) |
| 16 | C$_2$H$_5$ | n-C$_3$H$_7$ | n-C$_3$H$_7$ | 4 | C$_2$H$_5$ | diethyl trans-2-(3-oxo-4,4-dipropyl-1-nonenyl) |

EXAMPLE 17

Diethyl trans-2-(3-hydroxy-4,4-dimethyl-1-octenyl)cyclopropane-1,1-dicarboxylate (1; $R^1 = C_2H_5$, $R^2$ and $R^6 = H$ Sodium borohydride (0.19 g) is added to a solution of diethyl trans-2-(4,4-dimethyl-3-oxo-1-octenyl)cyclopropane-1,1-dicarboxylate (1.62 g), described in Example 3, in ethanol (2.5 ml) at 0° to 5°. After the addition the mixture is rendered neutral by the addition of acetic acid, diluted with ether and washed with water. The ether phase is dried (Na$_2$SO$_4$) and concentrated. The residue is dissolved in ethyl acetate-benzene (1:9) and the solution poured through a column of silica gel (50 g). The eluate is concentrated to give the title compound, $\nu_{max}^{film}$ 3500, 1706 cm$^{-1}$, nmr (CDCl$_3$) δ 2.6 (m, 1H), 3.78 (m, 1H), 4.21 (q, 4H), 5.28 (q, 1H), 5.9 (q, 1H).

In the same manner but replacing diethyl rans-2-(4,4-dimethyl-3-oxo-1-octenyl)cyclopropane-1,1-dicarboxylate with an equivalent amount of diethyl trans-2-(4-methyl-3-oxo-1-octenyl) cyclopropane-1,1-dicarboxylate, described in Example 3, diethyl trans-2-(3-hydroxy-4-methyl-1-octenyl)cyclopropane-1,1-dicarboxylate, $\nu_{max}^{film}$ 3500 cm$^{-1}$, is obtained.

By following the procedure of Example 17 and utilizing the appropriate compound of formula 15 then other compounds of formula 1 ($R^2 = H$) are prepared. Examples of such compounds of formula 1 are listed in Table II. In each case the compound of formula 15 used as starting material is noted by the Example in which it is prepared.

then with 10% sodium thiosulfate solution twice, again with saturated NaCl solution, dried (Na$_2$SO$_4$) and concentrated to give a greenish yellow oil. The oil is dissolved in ethyl acetate-benzene (3:17) and poured through a column of silica gel. The eluate is concentrated to yield the title compound, nmr (CDCl$_3$) δ 0.88 ($t, J = 5$, 3H), 2.45 ($q$, 2H), 4.13 ($q$, 2H), 5.14 ($2 \times d, J = 16.8$, 1H), 5.72 ($d, J = 16$, 1H).

In the same manner but replacing methyl magnesium iodide with an equivalent amount of ethyl magnesium chloride, or propyl magnesium bromide, diethyl trans-2-(3-ethyl-3-hydroxy-1-octenyl)-cyclopropane-1,1-dicarboxylate and diethyl trans-2-(3-hydroxy-3-propyl-1-octenyl)cyclopropane-1,1-dicarboxylate, are obtained, respectively.

In the same manner but replacing diethyl trans-2-(3-oxo-1-octenyl)cyclopropane-1,1-dicarboxylate with an

TABLE II

| EXAMPLE | NO. OF EXAMPLE IN WHICH STARTING MATERIAL OF FORMULA 15 IS PREPARED | PRODUCT: (PREFIX LISTED BELOW)-CYCLO-PROPANE-1,1-DICARBOXYLATE |
|---|---|---|
| 18 | 3 | dimethyl trans-2-(4-ethyl-3-hydroxy-1-heptenyl) |
| 19 | 3 | diethyl trans-2-3-hdyroxy-4-propyl-1-nonenyl) |
| 20 | 3 | dimethyl trans-2-(4-ethyl-3-hydroxy-1-decenyl) |
| 21 | 7 | diethyl trans-2-(3-hydroxy-4-methyl-1-heptenyl) |
| 22 | 8 | dimethyl trans-2-(3-hydroxy-4-methyl-1-nonenyl) |
| 23 | 9 | diethyl trans-2-(4-ethyl-3-hydroxy-1-octenyl) |
| 24 | 10 | dimethyl trans-2-(4-methyl-3-hydroxy-1-decenyl) |
| 25 | 11 | diethyl trans-2-(3-hydroxy-4-propyl-1-heptenyl) |
| 26 | 12 | dimethyl trans-2-(3-hydroxy-4-ethyl-1-nonenyl |
| 27 | 13 | dipropyl trans-2-(3-hydroxy-4,4-dimethyl-1-decenyl) |
| 28 | 14 | dipropyl trans-2-(4-ethyl-3-hydroxy-4-methyl-1-decenyl) |
| 29 | 15 | dimethyl trans-2-(3-hydroxy-4-metyl-4-propyl-1-heptenyl) |
| 30 | 16 | diethyl trans-2-(3-hydroxy-4,-4-dipropyl-1-nonenyl) |

EXAMPLE 31

Diethyl trans-2-(3-hydroxy-3-methyl-1-octenyl)cyclopropane-1,1-dicarboxylate (1; $R^1 = C_2H_5$; $R^2$, $R^4$ and $R^5 = H$, $R^6 = CH_3$ and $n = 3$)

A solution of the lower alkyl magnesium halide, methyl magnesium iodide, prepared from 24.31 g of magnesium turnings and 157 g of methyl iodide in 1000 ml of ether, is cooled to −70°. Diethyl trans-2-(3-oxo-1-octenyl)cyclopropane-1,1-dicarboxylate (124.2 g); described in Example 3, in 600 ml ether is added slowly taking care that reaction mixture temperature does not exceed −45°. The mixture is stirred 75 min. at the temperature range −50° to −45°. Aqueous saturated NH$_4$Cl solution is added slowly keeping the temperature of the reaction mixture below −55°. The mixture is diluted with water and extracted with 1500 ml ether. The ether layer is washed with saturated NaCl solution twice, equivalent amount of diethyl trans-2-(4-methyl-3-oxo-1-octenyl)cyclopropane-1,1-dicarboxylate, described in Example 3 and using methyl magnesium iodide, ethyl magnesium chloride or propyl magnesium bromide as the lower alkyl magnesium halide, diethyl trans-2-(3-hydroxy-3,4-dimethyl-1-octenyl)cyclopropane-1,1-dicarboxylate, diethyl trans-2-(3-ethyl-3-hydroxy-4-methyl-1-octenyl)cyclopropane-1,1-dicarboxylate and diethyl trans-2-(3-hydroxy-4-methyl-3-propyl-1-octenyl)-cyclopropane-1,1-dicarboxylate, are obtained, respectively.

By following the procedure of Example 31 and utilizing the appropriate lower alkyl magnesium halide and compound of formula 15, for example those described in Examples 4 to 12, then other compounds of formula 1 in which $R^6$ is lower alkyl are obtained. Examples of such compounds of formula 1 are listed in Table III together with the requisite lower alkyl magnesium haide and the compound of formula 15.

TABLE III

| EXAMPLE | NO. OF EXAMPLE IN WHICH STARTING MATERIAL OF FORMULA 15 IS PREPARED | LOWER ALKYL MAGNESIUM HALIDE | PRODUCT: (PREFIX LISTED BELOW)-CYCLOPROPANE-1,1-DICARBOXYLATE |
|---|---|---|---|
| 32 | 4 | CH$_3$MgI | dimethyl trans-2-(3- |

TABLE III-continued

| EXAMPLE | NO. OF EXAMPLE IN WHICH STARTING MATERIAL OF FORMULA 15 IS PREPARED | LOWER ALKYL MAGNESIUM HALIDE | PRODUCT (PREFIX LISTED BELOW)-CYCLOPROPANE-1,1-DICARBOXYLATE |
|---|---|---|---|
| 33 | 5 | $C_2H_5MgBr$ | diethyl trans-2-(3-hydroxy-3-methyl-1-heptenyl) diethyl trans-2-(3-ethyl-3-hydroxy-1-nonenyl) |
| 34 | 6 | $n\text{-}C_3H_7MgCl$ | dimethyl trans-2-(3-hydroxy-3-propyl-1-decenyl) |
| 35 | 7 | $CH_3MgBr$ | diethyl trans-2-(3-hydroxy-3,4-dimethyl-1-heptenyl) |
| 36 | 8 | $C_2H_5MgCl$ | dimethyl trans-2-(3-ethyl-3-hydroxy-4-methyl-1-nonenyl) |
| 37 | 9 | $n\text{-}C_3H_7MgCl$ | diethyl trans-2-(4-ethyl-3-hydroxy-3-propyl-1-octenyl) |
| 38 | 10 | $CH_3MgI$ | dimethyl trans-2-(3-hydroxy-3,4-dimethyl-1-decenyl) |
| 39 | 11 | $C_2H_5MgCl$ | diethyl trans-2-(3-ethyl-3-hydroxy-4-propyl-1-heptenyl) |
| 40 | 12 | $n\text{-}C_3H_7MgCl$ | dimethyl trans-2-(4-ethyl-3-hydroxy-3-propyl-1-nonenyl) |

EXAMPLE 41

Diethyl trans-2-{3-[(tetrahydropyran-2-yl)oxy]-3-methyl-1-octenyl}cyclopropane-1,1-dicarboxylate (1; $R^1$ = $C_2H_5$, $R^2$ = (tetrahydropyran-2-yl)oxy, $R^4$ and $R^5$ = H, $R^6$ = $CH_3$ and $n$ = 3)

A solution of diethyl trans-2-(3-hydroxy-3-methyl-1-octenyl)cyclopropane-1,1-dicarboxylate (22.4 g), described in Example 31, dihydropyran (80 ml, distilled over sodium) and p-toluenesulfonic acid monohydrate (300 mg) is allowed to stand at room temperature for 30 min. After adding a few ml of 10% $Na_2CO_3$ solution the mixture is extracted with ether. The ether extract is washed with water, dried ($Na_2SO_4$) and evaporated. Purification of the residue by chromatography on silica gel gives the title compound, nmr ($CDCl_3$) δ 0.87 (t, 3H), 2.48 (m, 1H), 4.6 (1H), 5.5 (m, 2H).

In the same manner but using an equivalent amount of one of the compounds of formula 1 ($R^2$ = H), for example, the compounds listed in Examples 17 to 40, instead of diethyl trans-2-(3-hydroxy-3-methyl-1-octenyl)cyclopropane-1,1-dicarboxylate, then the corresponding tetrahydropyranyl ether compound of formula 1 ($R^2$ = tetrahydropyranyl) is obtained, for example, the corresponding tetrahydropyranyl ether compounds of Examples 17 to 40, respectively. More specifically exemplifed, in the same manner diethyl trans-2-(3-hydroxy-4-methyl-1-octenyl)cyclopropane-1,1-dicarboxylate, described in Example 17 gives diethyl trans-2-{3-[(tetrahydropyran-2-yl)oxy]-4-methyl-1-octenyl}-cyclopropane-1,1-dicarboxylate, $v_{max}^{film}$ 1035, 1140, 1220 cm$^{-1}$, and dimethyl trans-2-(4-ethyl-3-hydroxy-1-decenyl)cyclopropane-1,1-dicarboxylate, described in Example 24, gives dimethyl trans-2-{4-ethyl-3-[(tetrahydropyran-2-yl)oxy]-1-decenyl}-cyclopropane-1,1-dicarboxylate.

EXAMPLE 42

Dimethyl trans-1-(Carbomethoxymethyl)-5-(3-hydroxy-1-octenyl)-2-oxo-1,3-cyclopentanedicarboxylate (3; $R^1$ and $R^3$ = $CH_3$, $R^2$, $R^4$, $R^5$ and $R^6$ = H and $n$ = 3)

A solution of sodium methoxide (5 g of sodium dissolved in 150 ml of methanol) is added at room temperature to a solution of tiethyl 1,1,2-ethanetricarboxylate. The mixture is heated to 80° and a solution of the compound of formula 1, dimethyl trans-2-{3-[(tetrahydropyran-2-yl)oxy]-1-octenyl}cyclopropane-1,1-dicarboxylate, described by Abraham, cited above, is added slowly. The mixture is stirred for 1 hr. The methanol is removed under reduced pressure and the residue heated at 110° for 1.5 hr. After cooling the mixture is acidified with acetic acid-water (25 ml, 1:1) and extracted with ether. The ether extract is washed with water, dried ($MgSO_4$) and concentrated to give dimethyl trans-1-(carbomethoxymethyl)-5-{3-[(tetrahydropyran-2-yl)oxy]-1-octenyl}-2-oxo-1,3-cyclopentanedicarboxylate, $v_{max}^{EtOH}$ 290 nm (ε = 13,500) in the presence of a base. [Note: Transesterification of the ester groups has occurred during the preceding condensation. If desired this can be avoided by the substitution of ethanol for methanol.]

A mixture of the latter hydroxy protected derivative (95.1 g) in 375 ml of methanol-water (9:1) and p-toluenesulfonic acid monohydrate (2.85g) is stirred for 1 hr at room temperature. The mixture is rendered neutral by the addition of 10% $Na_2CO_3$. The methanol is removed by distillation. The residue is extracted with ether. The organic extract is washed with water until neutral, dried ($MgSO_4$) and concentrated. The residue is subjected to chromatography on $SiO_2$ using 20% ethyl acetate as eluant. Evaporation of the eluate gives the title compound $v_{max}^{EtOH}$ 289 nm (14,500) in the presence of base.

EXAMPLE 43

Dimethyl trans-1-(Carboethoxymethyl)-5-(3-hydroxy-3-methyl-1-octenyl)-2-oxo-1,3-cyclopentanedicarboxylate (3; $R^1$, $R^3$ and $R^6$ = $CH_3$, $R^2$, $R^4$ and $R^5$ = H and $n$ = 3)

To a solution of triethyl 1,1,2-ethanetricarboxylate (1.36 g) in 3 ml of methanol, a freshly prepared solution of sodium methoxide (from 0.126 g of sodium and 6 ml of absolute methanol) is added. The mixture is heated to 80°. A solution of dimethyl trans-(3-methyl-3-hydroxy-1-octenyl)cyclopropane-1-1-dicarboxylate (1.7 g) is gradually added and the resulting mixture stirred for an additional 15 min. The methanol is removed by distillation at reduced pressure. The residue is then heated at 100° for 45 min. Thereafter the mixture is cooled in an ice bath and rendered neutral with acetic acid. The mixture is extracted with ether. The extract is dried ($Na_2SO_4$) and concentrated. Chromatography of the residue on silica gel using ethyl acetate-benzene (1:4) as eluant gives the title compound, $\nu_{max}^{film}$ 3350, 1727 $cm^{-1}$.

By following the procedures of Examples 42 and 43 and using the appropriate compounds of formulae 1 and formula 2 as starting materials, other cyclopentanonetriesters of formula 3 are obtained.

For example, the use of the compound of formula 1, diethyl trans-2-{3-[(tetrahydropyran-2-yl)oxy]-3-methyl-1-octenyl}-cyclopropane-1,1-dicarboxylate, described in Example 41, and the compound of formula 2, triethyl ethane-1,1,2-tricarboxylate, in the procedure of Example 42 gives dimethyl trans-1-(carboethoxymethyl)-5-(3-hydroxy-3-methyl-1-octenyl)-2-oxo-1,3-cyclopentanedicarboxylate, identical to the product of Example 43, via the intermediate dimethyl trans-1-(carboethoxymethyl)-5-{3-[(tetrahydropyran-2-yl)oxy]-3-methyl-1-octenyl}-2-oxo-1,3-cyclopentanedicarboxylate, $\nu_{max}^{film}$ 1730 $cm^{-1}$.

Likewise, the use of diethyl trans-2-{3-[(tetrahydropyran-2-yl)oxy]-4,4-dimethyl-1-octenyl}cyclopropane-1,1-dicarboxylate and triethyl ethane-1,1,2-tricarboxylate gives dimethyl trans-1-(carbomethoxymethyl)-5-(3-hydroxy-4,4-dimethyl-1-octenyl)-2-oxo-1,3-cyclopentanedicarboxylate, $\nu_{max}^{film}$ 3500 $cm^{-1}$, $\nu_{max}^{EtOH}$ 291 nm ($\epsilon$ = 13,600) in the presence of base (NaOH).

Additional examples of compounds of formula 3 are listed in Table III together with the requisite starting materials. It is to be noted that when the procedure of Example 42 is used the requisite starting material of formula 1 is the corresponding tetrahydropyran-2-yl ether derivative of the compound of formula 4 noted therein; the tetrahydropyran-2-yl ether being prepared by following the procedure described in Example 41.

TABLE III

| EX. | NO. OF THE EXAMPLE IN WHICH STARTING MATERIAL OF FORMULA 1 IS DESCRIBED | STARTING MATERIAL OF FORMULA 2 $R^3$ | PRODUCT (PREFIX LISTED BELOW)-2-OXO-1,3-CYCLO-PENTANEDICARBOXYLATE |
|---|---|---|---|
| 44 | 18 | $CH_3$ | dimethyl trans-1-(carbomethoxymethyl)-5-(4-ethyl-3-hydroxy-1-heptenyl) |
| 45 | 19 | $C_2H_5$ | diethyl trans-1-(carboethoxymethyl)-5-(3-hydroxy-4-propyl-1-nonenyl) |
| 46 | 20 | $CH_3$ | dimethyl trans-1-(carbomethoxymethyl)-5-(4-ethyl-3-hydroxy-1-decenyl) |
| 47 | 21 | $C_2H_5$ | diethyl trans-1-(carboethoxymethyl)-5-(3-hydroxy-4-methyl-1-heptenyl) |
| 48 | 22 | $CH_3$ | dimethyl trans-1-(carbomethoxymethyl)-5-(3-hydroxy-4-methyl-1-nonenyl) |
| 49 | 23 | $C_2H_5$ | diethyl trans-1-(carboethoxymethyl)-5-(4-ethyl-3-hydroxy-1-octenyl) |
| 50 | 24 | $CH_3$ | dimethyl trans-1-(carbomethoxymethyl)-5-(4-methyl-3-hydroxy-1-decenyl) |
| 51 | 25 | $C_2H_5$ | diethyl trans-1-(carboethoxymethyl)-5-(3-hydroxy-4-propyl-1-heptenyl) |
| 52 | 26 | $CH_3$ | dimethyl trans-1-(carbomethoxymethyl)-5-(3-hydroxy-4-ethyl-1-nonenyl) |
| 53 | 27 | n-$C_3H_7$ | dipropyl trans-1-(carbopropoxymethyl)-5-(3-hydroxy-4,4-dimethyl-1-decenyl) |
| 54 | 28 | n-$C_3H_7$ | dipropyl trans-1-(carbopropoxymethyl)-5-(4-ethyl-3-hydroxy-4-methyl-1-decenyl) |
| 55 | 29 | $CH_3$ | dimethyl trans-1-(carbomethoxymethyl)-5-(3-hydroxy-4-methyl-4-propyl-1-heptenyl) |
| 56 | 30 | $C_2H_5$ | diethyl trans-1-(carboethoxymethyl)-5-(3-hydroxy-4,4-dipropyl-1-nonenyl) |
| 57 | 32 | $CH_3$ | dimethyl trans-1-(carbomethoxymethyl)-5-(3-hydroxy-3-methyl-1-heptenyl) |
| 58 | 33 | $C_2H_5$ | diethyl trans-1-(carboethoxymethyl)-5-(3-ethyl-3-hydroxy-1-nonenyl) |

TABLE III-continued

| EX. | NO. OF THE EXAMPLE IN WHICH STARTING MATERIAL OF FORMULA 1 IS DESCRIBED | STARTING MATERIAL OF FORMULA 2 R³ | PRODUCT: (PREFIX LISTED BELOW)-2-OXO-1,3-CYCLO-PENTANEDICARBOXYLATE |
|---|---|---|---|
| 59 | 34 | CH₃ | dimethyl trans-1-(carbomethoxymethyl)-5-(3-hydroxy-3-propyl-1-decenyl) |
| 60 | 35 | C₂H₅ | diethyl trans-1-(carboethoxymethyl)-5-(3-hydroxy-3,4-dimethyl-1-heptenyl) |
| 61 | 36 | CH₃ | dimethyl trans-1-(carbomethoxymethyl)-5-(3-ethyl-3-hydroxy-4-methyl-1-nonenyl) |
| 62 | 37 | C₂H₅ | diethyl trans-1-(carboethoxymethyl)-5-(4-ethyl-3-hydroxy-3-propyl-1-octenyl) |
| 63 | 38 | CH₃ | dimethyl trans-1-(carbomethoxymethyl)-5-(3-hydroxy-3,4-dimethyl-1-decenyl) |
| 64 | 39 | C₂H₅ | dietyl trans-1-(carboethoxymethyl)-5-(3-ethyl-3-hydroxy-4-propyl-1-heptenyl) |
| 65 | 40 | CH₃ | dimethyl trans-1-(carbomethoxymethyl)-5-(4-ethyl-3-hydroxy-3-propyl-1-nonenyl) |

EXAMPLE 66 trans-2-(3-Hydroxy-1-octenyl)-5-oxocyclopentaneacetic acid (4; $R^2$, $R^4$, $R^5$ and $R^6$ = H and $n = 3$)

A suspension of dimethyl trans-1-(carbomethoxymethyl)-5-(3-hydroxy-1-octenyl)-2-oxo-1,3-cyclopentanedicarboxylate (26.24 g), described in Example 42, in a solution of sodium hydroxide (12 g) in 70 ml of water and 80 ml of methanol is heated at reflux for 2 hr. The reaction mixture is cooled, acidified to pH 6 with 2N HCl. The resulting oil is extracted with ether. The ether extract is washed with water, dried (MgSO₄) and the solvent removed. The residue is subjected to chromatography on silica gel (850 g). Elution with methanol-chloroform (1:9) yields the title compound, $\nu_{max}^{film}$ 3350, 1727 cm⁻¹. The corresponding methyl ester of the title compound, prepared by treatment with diazomethane, has $\nu_{max}^{film}$ 3412, 1737 cm⁻¹.

By following the procedure of Example 66 and using the appropriate cyclopentanonetriester of formula 3, for example those described in Examples 43 to 65, other compounds of formula 4 are obtained.

For example, the use of the cyclopentanonetriester of formula 3, dimethyl trans-1-(carboethoxymethyl)-5-(3-hydroxy-3-methyl-1-octenyl)-2-oxo-1,3-cyclopentanedicarboxylate, described in Example 43, in the procedure of Example 66, gives trans-2-(3-hydroxy-3-methyl-1-octenyl)-5-oxocyclopentaneacetic acid, $\nu_{max}^{film}$ 3350, 1727 cm⁻¹.

Likewise, the use of dimethyl trans-1-(2-carbomethoxymethyl)-5-(3-hydroxy-4,4-dimethyl-1-octenyl)-2-oxo-1,3-cyclopentanedicarboxylate, described in Example 43, gives trans-2-(3-hydroxy-4,4-dimethyl-1-octenyl)-5-oxocyclopentaneacetic acid, $\nu_{max}^{film}$ 3355, 1729 cm⁻¹.

Further examples of such compounds of formula 4 are listed in Table IV together with the requisite cyclopentanonetriesters starting material, the latter compound being noted by the example describing its preparation.

TABLE IV

| EXAMPLE | NO. OF EXAMPLE IN WHICH CYCLOPENTANONETRIESTER OF FORMULA 3 IS PREPARED | PRODUCT: |
|---|---|---|
| 67 | 44 | trans-2-(4-ethyl-3-hydroxy-1-heptenyl)-5-oxocyclopentaneacetic acid |
| 68 | 45 | trans-2-(3-hydroxy-4-propyl-1-nonenyl)-5-oxocyclopentaneacetic acid |
| 69 | 46 | trans-2-(4-ethyl-3-hydroxy-1-decenyl)-5-oxocyclopentaneacetic acid |
| 70 | 47 | trans-2-(3-hydroxy-4-methyl-1-heptenyl)-5-oxocyclopentaneacetic acid |
| 71 | 48 | trans-2-(3-hydroxy-4-methyl-1-nonenyl)-5-oxocyclopentaneacetic acid |
| 72 | 49 | trans-2-(4-ethyl-3-hydroxy-1-octenyl)-5-oxocyclopentaneacetic acid |
| 73 | 50 | trans-2-(4-methyl-3-hydroxy-1-decenyl)-5-oxocyclopentaneacetic acid |
| 74 | 51 | trans-2-(3-hydroxy-4-propyl-1-heptenyl)-5-oxocyclopentaneacetic acid |
| 75 | 52 | trans-2-(3-hydroxy-4-ethyl-1-nonenyl)-5-oxocyclopentaneacetic acid |
| 76 | 53 | trans-2-(4,4-dimethyl-3-hydroxy-1-decenyl)-5-oxocyclopentaneacetic acid |
| 77 | 54 | trans-2-(4-ethyl-4-methyl-3-hydroxy-1-decenyl)-5-oxocyclopentaneacetic acid |
| 78 | 55 | trans-2-(4-methyl-3-hydroxy-4-propyl-1-heptenyl)-5-oxocyclopentaneacetic |

TABLE IV-continued

| EXAMPLE | NO. OF EXAMPLE IN WHICH CYCLOPENTANONETRIESTER OF FORMULA 3 IS PREPARED | PRODUCT: |
|---|---|---|
| 79 | 56 | trans-2-(3-hydroxy-4,4-dipropyl-1-nonenyl)-5-oxocyclopentaneacetic acid |
| 80 | 57 | trans-2-(3-hydroxy-3-methyl-1-heptenyl)-5-oxocyclopentaneacetic acid |
| 81 | 58 | trans-2-(3-ethyl-3-hydroxy-1-nonenyl)-5-oxocyclopentaneacetic acid |
| 82 | 59 | trans-2-(3-hydroxy-3-propyl-1-decenyl)-5-oxocyclopentaneacetic acid |
| 83 | 60 | trans-2-(3-hydroxy-3,4-dimethyl-1-heptenyl)-5-oxocyclopentaneacetic acid |
| 84 | 61 | trans-2-(3-ethyl-3-hydroxy-4-methyl-1-nonenyl)-5-oxocyclopentaneacetic acid |
| 85 | 62 | trans-2-(4-ethyl-3-hydroxy-3-propyl-1-octenyl)-5-oxocyclopentaneacetic acid |
| 86 | 63 | trans-2-(3-hydroxy-3,4-dimethyl-1-decenyl)-5-oxocyclopentaneacetic acid |
| 87 | 64 | trans-2-(3-ethyl-3-hydroxy-4-propyl-1-heptenyl)-5-oxocyclopentaneacetic acid |
| 88 | 65 | trans-2-(4-ethyl-3-hydroxy-3-propyl-1-nonenyl)-5-oxocyclopentaneacetic acid |

EXAMPLE 89 trans-2-{3-[(Tetrahydropyran-2-yl)oxy]-1-octenyl}-5-oxocyclopentaneacetic acid (4; $R^2 =$ tetrahydropyran-2-yloxy, $R^4$, $R^5$ and $R^6 = H$ and $n = 3$)

To a solution of trans-2-(3-hydroxy-1-octenyl)-5-oxocyclopentaneacetic acid (4.7 g), described in Example 66, in methylene chloride (20 ml) at −20° is added dihydropyran (1.61 g) and p-toluenesulfonic acid (0.04 g). The mixture is stirred at that temperature for 30 minutes. A further qunatity of p-toluenesulfonic acid (0.07 g) is added and the mixture maintained at the same temperature for 1 hr. The reaction mixture is diluted with ether, washed with water, dried (MgSO$_4$) and the solvent removed. The residue is passed through a column of silica gel (300 g) in a solution of 5% methanol-chloroform. The eluate is concentrated to give the title compound, $\nu_{max}^{film}$ 1727 cm$^{-1}$, nmr (CDCl$_3$) δ 0.88 (t, 3H), 4.69 (m, 1H), 5.5 (m, 2H).

In the same manner but using an equivalent amount of one of the other compounds of formula 4 ($R^2 = H$), for example the compound listed in Examples 67 to 81, instead of trans-2-(3-hydroxy-1-octenyl)-5-oxocyclopentaneacetic acid, then the corresponding tetrahydropyranyl ether compound of formula 4 ($R^2 =$ tetrahydropyran-2-yl) is obtained; for example, the use of trans-2-(3-hydroxy-4,4-dimethyl-1-octenyl)-5-oxocyclopentaneacetic acid, described in Example 66, gives trans-2-{4,4-dimethyl-3-[(tetrahydropyran-2-yl)oxy]-1-octenyl}-5-oxocyclopentaneacetic acid, $\nu_{max}^{film}$ 1727 cm$^{-1}$.

EXAMPLE 90 trans-2β-Hydroxy-5-{3-[(tetrahydropyran-2-yl)oxy]-1-octenyl}cyclopentaneacetic acid (5; $R^2 =$ tetrahydropyran-2-yloxy, $R^4$, $R^5$ and $R^6 = H$ and $n = 3$) and
trans-2α-hydroxy-5-{3-[(tetrahydropyran-2-yl)oxy]-1-octenyl}cyclopentaneacetic acid γ-lactone (6; $R^2 =$ tetrahydropyran-2-yloxy, $R^4$, $R^5$ and $Rk^6 = H$ and $n = 3$)

To a solution of trans-2-{3-[(tetrahydropyran-2-yl)oxy]-1-octenyl}-5-oxocyclopentaneacetic acid (5.1 g), described in Example 89, in methanol (10 ml), cooled to −10°, is added a solution of sodium (0.354 g) in methanol (5 ml). Thereafter, sodium borohydride (0.152 g) is added to the mixture. The mixture is stirred for 1 hr, diluted with ether and rendered acidic wick cone. HCl to pH 4.5. The ether layer is separated. The aqueous phase is extracted with fresh ether. The combined ether layers are washed quickly with water, dried (MgSO$_4$) and concentrated to yield a mixture of the title compounds in about a 7:3 ratio by weight.

The two compounds can be separated by dissolving the preceding mixture in methylene chloride extracting the acid 5 into an aqueous alkaline solution, for example, 5% Na$_2$CO$_3$, and subsequent acidification thereof gives the title compound of formula 5, $\nu_{max}^{film}$ 3200, 1700 cm$^{-1}$, nmr (CDCl$_3$) δ 0.88 (t, 3H), 4.7 (m, 1H), 5.6 (m, 2H). The corresponding γ-lactone 6 is described below.

The preceding mixture of the title compounds (4.0 g) in methylene dichloride (35 ml) and triethylamine (2.339 g) is cooled to −5° to −10°. A solution of methanesulfonyl chloride (1.44 g), in methylene chloride (15 ml) is added dropwise. The mixture is stirred at that temperature for 45 minutes. The mixtue is diluted with methylene chloride, washer with water (5X), dried (MgSO$_4$) and the solvent removed to yield a crude product which is poured through on a column of silica gel (250 g) in ethylacetate-benzene. Evaporation of the eluate gives the title compound of formula 6, $\nu_{max}^{film}$ 1762, 1030, 1012 cm$^{-1}$, nmr (CDCl$_3$) δ 4.68 (s, 1H), 5.01 (s, 1H), 5.5 (m, 2H).

By following the procedure of Example 90 and using the appropriate compound of formula 4, for example those described in Examples 66 to 89, other compounds of formulae 5 and 6 are obtained.

For example, the use of the compound of formula 4, trans-2-(3-hydroxy-3-methyl-1-octenyl)-5-oxocyclopentaneacetic acid, described in Example 66, gives trans-2α-hydroxy-5-(3-hydroxy-3-methyl-1-octenyl)-cyclopentaneacetic acid, and its corresponding γ-lactone, $\nu_{max}^{film}$ 3400, 1765 cm$^{-1}$.

Likewise, the use of trans-2-(3-hydroxy-4,4-dimethyl-1-octenyl)-5-oxocyclopentaneacetic acid, described in Example 66, gives trans-2α-hydroxy-5-(3-hydroxy-4,4-dimethyl-1-octenyl)cyclopentaneacetic acid, and its corresponding γ-lactone, $\nu_{max}^{film}$ 3450, 1765 cm$^{-1}$.

Further examples of the compounds of formula 5 and their corresponding γ-lactones of formula 6, which may be prepared by the procedure of Example 90, are listed in Table V. In each case the requisite starting material of formula 4 are noted by the example describing its preparation also in each case the corresponding tetrahydropyranyl ether of the starting material of formula 4 may replace the designated starting material.

TABLE IV

| EXAMPLE | NO. OF EXAMPLE IN WHICH STARTING MATERIAL OF FORMULA 4 IS PREPARED | PRODUCT: (PREFIX LISTED BELOW)-CYCLOPENTANEACETIC ACID, 5 (AND CORRESPONDING γ-LACTONE, 6) |
|---|---|---|
| 91 | 67 | trans-2α-hydroxy-5-(4-ethyl-3-hydroxy-1-heptenyl) |
| 92 | 68 | trans-2α-hydroxy-5-(3-hydroxy-4-propyl-1-nonenyl) |
| 93 | 69 | trans-2α-hydroxy-4-(4-ethyl-3-hydroxy-1-decenyl |
| 94 | 70 | trans-2α-hydroxy-5-(3-hydroxy-4-methyl-1-heptenyl) |
| 95 | 71 | trans-2α-hydroxy-5-(3-hydroxy-4-methyl-1-nonenyl) |
| 96 | 72 | trans-2α-hydroxy-5-(4-ethyl-3-hydroxy-1-octenyl) |
| 97 | 73 | trans-2α-hydroxy-5-(4-methyl-3-hydroxy-1-decenyl |
| 98 | 74 | trans-2α-hydroxy-5-(3-hydroxy-4-propyl-1-heptenyl) |
| 99 | 75 | trans-2α-hydroxy-5-(3-hydroxy-4-ethyl-1-nonenyl) |
| 100 | 76 | trans-2α-hydroxy-5-(4,4-dimethyl-3-hydroxy-1-decenyl) |
| 101 | 77 | trans-2α-hydroxy-5-(4-ethyl-4-methyl-3-hydroxy-1-decenyl) |
| 102 | 78 | trans-2α-hydroxy-5-(4-methyl-3-hydroxy-4-propyl-1-heptenyl) |
| 103 | 79 | trans-2α-hydroxy-5-(3-hydroxy-4,4-dipropyl-1-nonenyl) |
| 104 | 80 | trans-2α-hydroxy-5-(3-hydroxy-3-methyl-1-heptenyl) |
| 105 | 81 | trans-2α-hydrox-5-(3-ethyl-3-hydroxy-1-nonenyl) |
| 106 | 82 | trans-2α-hydroxy-5-(3-hydroxy-3-propyl-1-decenyl) |
| 107 | 83 | trans-2α-hydroxy-5-(3-hydroxy-3,4-dimethyl-1-heptenyl) |
| 108 | 84 | trans-2α-hydroxy-5-(3-ethyl-3-hydroxy-4-methyl-1-nonenyl) |
| 109 | 85 | trans-2α-hydroxy-5-(4-ethyl-3-hydroxy-3-propyl-1-octenyl) |
| 110 | 86 | trans-2α-hydroxy-5-(3-hydroxy-3,4-dimethyl-1-decenyl) |
| 111 | 87 | trans-2α-hydroxy-5-(3-ethyl-3-hydroxy-4-propyl-1-heptenyl) |
| 112 | 88 | trans-2α-hydroxy-5-(4-ethyl-3-hydroxy-3-propyl-1-nonenyl) |

EXAMPLE 113 trans-2α-Hydroxy-5-(3-hydroxy-1-octenyl)cyclopentaneacetic acid γ-lactone (6; $R^2$, $R^4$, $R^5$ and $R^6$ = H and $n = 3$)

trans-2α-Hydroxy-5-{3-[(tetrahydropyran-2-yloxy]-1-octenyl}-cyclopentaneacetic acid γ-lactone (2.0 g), described in Example 90, is dissolved in methanol (10 ml):and water (3.5 ml) containing p-toluenesulfonic acid (0.4 g). The mixture is stirred at room temperature for 30 minutes. The solvent is removed under reduced pressure. The residue is shaken between water and ether. The ether layer is dried (MgSO$_4$) and evaporated to give the title compound, $\nu_{max}^{film}$ 3450, 1765 cm$^{-1}$.

The corresponding DMIS ether of the title compound has $\nu_{max}^{film}$ 1765 cm$^{-1}$.

EXAMPLE 114 trans-2α-Hydroxy-5-(3-oxo-1-octenyl)cyclopentaneacetic acid γ-lactone (7; $R^4$ and $R^5$ = H and $n = 3$)

A solution of trans-2α-hydroxy-5-(3-hydroxy-1-octenyl)-cyclopentaneacetic acid γ-lactone (1.9 g), described in Example 113, in chloroform in (60 ml) is stirred with activated magnanise dioxide (14.9 g) at 40° (bath temperature) for 15 hr. The reaction mixture is filtered and the precipitate washed with hot chloroform. The combined chloroform solutions are evaporated. The residue is subjected to chromatography on silica gel using ethyl acetate-benzene (3:7) as eluant. Evaporation of the eluant gives the title compound, mp 36° to 36.5°C, $\nu_{max}^{CHCl_3}$ 1755, 1685, 1625 cm$^{-1}$.

By following the procedure of Example 114 and using the appropriate hydroxylactone of formula 6; for example, those of Examples 91 to 103, other compounds of formula 7 are obtained.

For example, the use of the compound of formula 6, trans-2α-hydroxy-5-(3-hydroxy-4,4-dimethyl-1-octenyl)cyclopentaneacetic acid γ-lactone, described in Example 90, gives trans-2α-hydroxy-5-(4,4-dimethyl-3-oxo-1-octenyl)cyclopentaneacetic acid γ-lactone, $\nu_{max}^{film}$ 1765, 1680, 1620 cm$^{-1}$.

Further examples of the compounds of formula 7 are listed in Table VI. In each case the requisite starting material of formula 6 is noted by the example describing its preparation.

TABLE VI

| EXAMPLE | NO. OF EXAMPLE IN WHICH STARTING MATERIAL OF FORMULA 6 IS PREPARED | PRODUCT: (PREFIX LISTED BELOW)-CYCLOPENTANEACETIC ACID γ-LACTONE |
|---|---|---|
| 115 | 91 | trans-2α-hydroxy-5-(4-ethyl-3-oxo-1-heptenyl) |
| 116 | 92 | trans-2α-hydroxy-5-(3-oxo-4-propyl-1-nonenyl) |
| 117 | 93 | trans-2α-hydroxy-5-(4-ethyl-3-oxo-1-decenyl) |
| 118 | 94 | trans-2α-hydroxy-5-(4-methyl-3-oxo-1-heptenyl) |
| 119 | 95 | trans-2α-hydroxy-5-(3-oxo-4-methyl-1-nonenyl) |
| 120 | 96 | trans-2α-hydroxy-5-(4-ethyl-3-oxo-1-octenyl) |
| 121 | 97 | trans-2α-hydroxy-5-(4-methyl-3-oxo-1-decenyl) |
| 122 | 98 | trans-2α-hydroxy-5-(3-oxo-4-propyl-1-heptenyl) |
| 123 | 99 | trans-2α-hydroxy-5-(4-ethyl-3-oxo-1-nonenyl) |
| 124 | 100 | trans-2α-hydroxy-5-(4,4-dimethyl-3-oxo-1-decenyl) |
| 125 | 101 | trans-2α-hydroxy-5-(4-ethyl-4-methyl-3-oxo-1-decenyl) |
| 126 | 102 | trans-2α-hydroxy-5-(4-methyl-3-oxo-4-propyl-1-heptenyl) |
| 127 | 103 | trans-2α-hydroxy-5-(3-oxo-4,4-dipropyl-1-nonenyl) |

EXAMPLE 128

2α-Hydroxy-5-(3-oxooctyl)cyclopentaneacetic acid γ-lactone (8; $R^4$ and $R^5 = H$ and $n = 3$)

A solution of trans-2α-hydroxy-5-(3-oxo-1-octenyl)-cyclopentaneacetic acid γ-lactone (5.0 g), described in Example 114, in methanol (100 ml) is hydrogenated in the presence of 10% palladiumcharcoal (1.0 g) at 25°.

After the uptake of the theoretical amount of hydrogen, the catalyst is collected on a filter and the filtrate is concentrated to yield the title compound, $\nu_{max}^{film}$ 1765, 1710 cm$^{-1}$.

By following the procedure of Example 128 and using the appropriate hydroxylactone of formula 7; other compounds of formula 8 are obtained.

For example the use of the compound of formula 7, trans-2α-hydroxy-5-(4,4-dimethyl-3-oxo-1-octenyl)cy-clopentaneacetic acid γ-lactone, described in Example 114, gives 2α-hydroxy-5-(4,4-dimethyl-3-oxooctyl)cyclopentaneacetic acid γ-lactone, $\nu_{max}^{film}$ 1770, 1700 cm$^{-1}$.

Further examples of the compound of formula 8 are listed in Table VIII. In each case the requisite starting material of formula 7 is noted by the example in which is is prepared.

TABLE VII

| EXAMPLE | NO. OF EXAMPLE IN WHICH STARTING MATERIAL OF FORMULA 7 IS PREPARED | PRODUCT: (PREFIX LISTED BELOW)-CYCLOPENTANEACETIC ACID γ-LACTONE |
|---|---|---|
| 129 | 115 | 2α-hydroxy-5-(4-ethyl-3-oxoheptyl) |
| 130 | 116 | 2α-hydroxy-5-(3-oxo-4-propylnonyl) |
| 131 | 117 | 2α-hydroxy-5-(4-ethyl-3-oxodecyl) |
| 132 | 118 | 2α-hydroxy-5-(4-methyl-3-oxoheptyl) |
| 133 | 119 | 2α-hydroxy-5-(4-methyl-3-oxononyl) |
| 134 | 120 | 2α-hydroxy-5-(4-ethyl-3-oxooctyl) |
| 135 | 121 | 2α-hydroxy-5-(4-methyl-3-oxodecyl) |
| 136 | 122 | 2α-hydroxy-5-(3-oxo-4-propylheptyl) |
| 137 | 123 | 2α-hydroxy-5-(4-ethyl-3-oxononyl) |
| 138 | 124 | 2α-hydroxy-5-(4,4-dimethyl-3-oxo-1-decyl) |
| 139 | 125 | 2α-hydroxy-5-(4-ethyl-4-methyl-3-oxodecyl) |
| 140 | 126 | 2α-hydroxy-5-(4-methyl-3-oxo-4-propylheptyl) |
| 141 | 127 | 2α-hydroxy-5-(3-oxo-4,4-dipropylnonyl) |

EXAMPLE 142

2α-Hydroxy-5-(3-hydroxyoctyl)cyclopentaneacetic acid γ-lactone (9; $R^2$, $R^4$, $R^5$ and $R^6 = H$ and $n = 3$)

By following the procedure of Example 17 but replacing diethyl trans-2-(4,4-dimethyl-3-oxo-1-octenyl)cyclopropane-1,1-dicarboxylate with an equivalent amount of 2α-hydroxy-5-(3-oxooctyl)cyclopentaneacetic acid γ-lactone, described in Example 128, the latter compound is reduced to give the title compound, $\nu_{max}^{film}$ 3400, 1770 cm$^{-1}$.

The title compound is also obtained by the procedure of Example 165.

By following the procedure of Example 142 and using the appropriate compound of formula 8, for example those in Examples 129 to 141, other compounds of formula 9 in which R$^6$ is hydrogen are obtained.

For example, the use of the compound of formula 8, 2α-hydroxy-5-(4,4-dimethyl-3-oxooctyl)cyclopentaneacetic acid γ-lactone, described in Example 128, 5, 3H), 1.13 (s, 3H), 1.67 (b, 1H), 2.33 and 2.71 (m, 2H), 500 (m, 1H).

By following the procedure of Example 149 and using the appropriate compound of formula 8, for example, those described in Examples 129 to 137, together with the appropriate lower alkyl magnesium halide, other compounds of formula 9 are obtained.

Further examples of the compound of formula 9 are listed in Table IX. In each case the requisite starting material of formula 8 is noted by the example in which it is prepared.

TABLE IX

| EXAMPLE | NO. OF EXAMPLE IN WHICH STARTING MATERIAL OF FORMULA 8 IS PREPARED | LOWER ALKYL MAGNESIUM HALIDE | PRODUCT: (PREFIX LISTED BELOW)-CYCLOPENTANEACETIC ACID, 5 (AND CORRESPONDING γ-LACTONE, 6 |
|---|---|---|---|
| 150 | 129 | CH$_3$MgI | 2α-hydroxy-5-(4-ethyl-3-hydroxy-3-methylheptyl) |
| 151 | 130 | C$_2$H$_5$MgBr | 2α-hydroxy-5-(3-ethyl-3-hydroxy-4-propylnonyl) |
| 152 | 131 | n-C$_3$H$_7$MgCl | 2α-hydroxy-5-(4-ethyl-3-hydroxy-3-propyldecyl) |
| 153 | 132 | C$_2$H$_5$MgCl | 2α-hydroxy-5-(3-ethyl-3-hydroxy-4-methylheptyl) |
| 154 | 133 | CH$_3$MgI | 2α-hydroxy-5-(3-hydroxy-3,4-dimethylnonyl) |
| 155 | 134 | C$_2$H$_5$MgI | 2α-hydroxy-5-(3,4-diethyl-3-hydroxyoctyl) |
| 156 | 135 | n-C$_3$H$_7$MgI | 2α-hydroxy-5-(3-hydroxy-4-methyldecyl) | gives 2α-hydroxy-5-(3-hydroxy-4,4-dimethylocytl)cyclopentaneacetic acid γ-lactone.

Further examples of the compound of formula 9 in which R$^6$ is hydrogen are listed in Table VIII. In each case the requisite starting material of formula is noted by the example in which it is prepared.

TABLE VIII

| EXAMPLE | NO. OF EXAMPLE IN WHICH STARTING MATERIAL OF FORMULA 4 IS PREPARED | PRODUCT: (PREFIX LISTED BELOW)-CYCLOPENTANEACETIC ACID, 5 (AND CORRESPONDING γ-LACTONE, 6) |
|---|---|---|
| 143 | 136 | 2α-hydroxy-5-(3-hydroxy-4-propylheptyl) |
| 144 | 137 | 2α-hydroxy-5-(4-ethyl-3-hydroxynonyl) |
| 145 | 138 | 2α-hydroxy-5-(4,4-dimethyl-3-hydroxy-1-decyl) |
| 146 | 139 | 2α-hydroxy-5-(4-ethyl-3-hydroxy-4-methyldecyl) |
| 147 | 140 | 2α-hydroxy-5-(3-hydroxy-4-methyl-4-propylheptyl) |
| 148 | 141 | 2α-hydroxy-5-(3-hydroxy-4,4-dipropylnonyl) |

EXAMPLE 149

2α-Hydroxy-5-(3-hydroxy-3-methyloctyl)cyclopentaneacetic acid γ-lactone (9; R$^2$, R$^4$ and R$^5$ = H, R$^6$ = CH$_3$ and n = 3)

A solution of 2α-hydroxy-5-(3-oxooctyl)cyclopentaneacetic acid γ-lactone (6.66 g), described in Example 128, in ether (100 ml) is treated dropwise with the lower alkyl magnesium halide, methyl magnesium iodide (1.5 molar in ether, 33 ml) while keeping the reaction temperature at 0°. The Grignard complex is then decomposed with 10% ammonium chloride solution. The reaction mixture is extracted with ether, washed with brine, dried (Na$_2$SO$_4$) and concentrated. The residue in ethyl acetate-benzene (2:8) is poured through a column of silica gel. Evaporation of the eluate gives the title compound, nmr (CDCl$_3$) δ0.9 (t, J =

EXAMPLE 157 trans-2α-Hydroxy-5-(3-hydroxy-3-methyl-1-octenyl)-cyclopentaneacetic acid γ-lactone (12; R$^2$, R$^4$ and R$^5$ = H, R$^6$ = CH$_3$ and n = 3)

By following the procedure of Example 149, but replacing 2α-hydroxy-5-(3-oxooctyl)cyclopentaneacetic acid γ-lactone, with an equivalent amount of trans-2α-hydroxy-5-(3-oxo-1-octenyl)cyclopentaneacetic acid γ-lactone, described in Example 114, the title compound is obtained, $\nu_{max}^{film}$ 3420, 1770 cm$^{-1}$, nmr (CDCl$_3$) δ0.9 (t, J = 5, 3H), 1.26 (3H), 1.7 (1H), 5.05 (m, 1H), 5.65 (m, 2H).

By following the procedure of Example 157 and using the appropriate compound of formula 7, for example, those described in Examples 115–123, together with the appropriate lowe alkyl magnesium halide, other compounds of formula 12 are obtained.

Further examples of the compound of formula 12 are listed in Table X. In each case the requisite starting material of formula is noted by the example in which it is prepared.

TABLE X

| EXAMPLE | NO. OF EXAMPLE IN WHICH STARTING MATERIAL OF FORMULA 7 IS PREPARED | LOWER MAGNESIUM HALIDE | PRODUCT: (PREFIX LISTED BELOW)-CYCLOPENTANEACETIC ACID, 5 (AND CORRESPONDING γ-LACTONE, 6 |
|---|---|---|---|
| 158 | 115 | $CH_3MgBr$ | trans-2α-hydroxy-5-(4-ethyl-3-hydroxy-4-propyl-1-nonenyl) |
| 159 | 116 | $C_2H_5MgBr$ | trans-2α-hydroxy-5-(3-ethyl-3-hydroxy-4-propyl-1-nonenyl) |
| 160 | 117 | $n-C_3H_7MgCl$ | trans-2α-hydroxy-5-(4-ethyl-3-hyroxy-3-propyl-1-decenyl) |
| 161 | 118 | $C_2H_5MgCl$ | trans-2α-hydroxy-5-(3-ethyl-3-hydroxy-4-methyl-1-heptenyl) |
| 162 | 119 | $CH_3MgI$ | trans-2α-hydroxy-5-(4-hydroxy-3,4-dimethyl-1-nonenyl) |
| 163 | 120 | $C_2H_5MgI$ | trans-2α-hydroxy-5-(3,4-diethyl-3-hydroxy-1-octenyl) |
| 164 | 121 | $CH_3MgI$ | trans-2α-hydroxy-5-(3-hydroxy-3,4-dimethyl-1-decenyl) |

EXAMPLE 165

2α-Hydroxy-5-(3-hydroxyoctyl)cyclopentaneacetic acid γ-lactone (9, $R^2$, $R^4$, $R^5$ and $R^6$ = H and $n$ = 3)

The title compound is obtained, in a addition to the procedure of Example 142, by hydrogenation of the compound of formula 6 ($R^6$ = H), trans-2α-hydroxy-5-(3-hydroxy-1-octenyl)cyclopentaneacetic acid γ-lactone, described in Example 113, by the procedure of R. D. Hoffsommer, et al, *Tetrahedron Letters*, 4085 (1971), using Raney nickel in dioxane.

By following the procedure of Example 165 and using the appropriate compound of formula 6 ($R^6$=H), for Example those described in Examples 90 to 112, other corresponding compounds of formula 9 ($R^6$ = H) are obtained.

Further examples of the compounds of formula 9 are listed in Table XI. In each case the requisite starting material of formula 6 is noted by the example in which it is prepared.

TABLE XI

| EXAMPLE | NO. OF EXAMPLE IN WHICH STARTING MATERIAL OF FORMULA 4 IS PREPARED | PRODUCT: (PREFIX LISTED BELOW)-CYCLOPENTANEACETIC ACID, 5 (AND CORRESPONDING γ-LACTONE, 6) |
|---|---|---|
| 166 | 99 | 2α-hydroxy-5-(3-hydroxy-4-ethylnonyl) |
| 167 | 100 | 2α-hydroxy-5-(4,4-dimethyl-3-hydroxydecyl) |
| 168 | 101 | 2α-hydroxy-5-(4-ethyl-4-methyl-3-hydroxydecyl) |
| 169 | 102 | 2α-hydroxy-5-(4-methyl-3-hydroxy-4-propylheptyl) |
| 170 | 103 | 2α-hydroxy-5-(3-hydroxy-4,4-dipropylnonyl) |
| 171 | 104 | 2α-hydroxy-5-(3-hydroxy-3-methylheptyl) |
| 172 | 108 | 2α-hydroxy-5-(3-ethyl-3-hydroxy-4-methylnonyl) |
| 173 | 109 | 2α-hydroxy-5-(4-ethyl-3-hydroxy-3-propyloctyl) |

EXAMPLE 174

Hexahydro-2-hydroxy-4-[3-(dimethyl-tert-butylsilyloxy)-1-octenyl]-2H-cyclopenta[b]furan (13; $R^2$, $R^4$, $R^5$ and $R^6$ = H and $n$ = 3).

A solution of the compound of formula 6, trans-2α-hydroxy-5-(3-hydroxy-1-octenyl)cyclopentaneacetic acid γ-lactone, in the form of its dimethyl-tert-butylsilyl ether, (6.66 g), described in Example 113, in dry toluene (40 ml) is cooled to −75°C. As solution of diisobutyl aluminum hydride (3.9 g in 10.8 ml. of hexane) is added by syringe under a nitrogen atmosphere. The mixture is stirred afor 15 minutes at that temperature and then diluted with ether, washed with water. The gelantinous aluminum salts are removed by filtration. The filtrate is washed with water (2X), dried ($MgSO_4$) and the solvent is removed to give the title compound, γ 3360 cm$^{-1}$, nmr ($CDCl_3$) δ 4.02 (m, 1H), 4.63 (m, 1H), 5.42 (m, 2H).

EXAMPLE 175 trans, cis-7-[2α-Hydroxy-5-(3-hydroxy-1-octenyl)cyclopentyl]-5-heptenoic acid (11; $R^2$, $R^4$, $R^5$, $R^6$ and $R^7$ = H, X = OH, Y = H, Z = trans CH = CH, $m$ = 3 and $n$ = 3)

To a suspension of sodium hydride (7.42 g, 57% in oil) washed with hexane, is added dry dimethyl sulfoxide (45 ml). The mixture is heated to 75° to 80° (bath temperature) for 1 hour. By this all the sodium hydride has reacted. The mixture is cooled. A solution of the phosphonium bromide, (39.0 g) derived from triphenylphosphine and ω-bromo pentanoic acid, in dry DMSO (90 ml) is added gradually to the solution of sodio methylsulfinyl carbinide; followed by the addition of a solution of the hemiacetal of formula 13, hexahydro-2α-hydroxy-4-[3-(dimethyl-tert-butylsilloxy)-1-octenyl)]-2H-cyclopenta[b]furan (5.42 g), described in Example 174, in dry dimethylsulfoxide (15 ml). The mixture is stirred overnight at room temperature. The reaction mixture is diluted with water, acidified with acetic acid (5 ml), and extracted with ether. The ether extract is washed with water, dried ($Na_2SO_4$) and the solvent is removed. The residue is passed through a column of silica gel (400 g) using ether-hexane (1:1) as eluant. Evaportion of the eluate gives the corresponding dimethylisopropylsilyl ether of the title compound, $\nu_{max}^{film}$ 3470, 1710 cm$^{-1}$.

Removal of the hydroxy protecting group:

The latter compound (4.1) g is dissolved in methanol (20 ml) and water (7 ml) containing p-toluene sulfonic acid (0.4 g). The reaction mixture is stirred for 30 minutes, the solvent is removed under reduced pressure. The residue is extracted with ether. The extract is washed with water, dried ($MgSO_4$) the solvent is evaporated. Purification by chromatography of the residue [$SiO_2$, benzene-ethyl acetate (9:1)] gives the title compound as a mixture of stereochemical isomers with respect to the asymmetric carbon atom in the side chain to which the hydroxyl is attached. The mixture has $\nu_{max}^{film}$ 3480, 1700 cm$^{-1}$, nmr (CDCl$_3$) δ 0.87 (m, 3H), 4.18 (m, 2H), 5.45 (m, 4H), identical to the mixture of the same name described in copending U.S. application Ser. No. 238,650, filed Mar. 27, 1972.

By following sequentically the procedure of Examples 174 and 175, and using the appropriate compound of formula 6 or 9, for example, those of Examples 90 to 112 other prostaglandin derivatives of formula 11 are obtained.

For example the use of the compound of formula 6, trans-2α-hydroxy-5-(3-hydroxy-3-methyl-1-octenyl)-cyclopentaneacetic acid γ-lactone, described in Example 90, gives trans,cis-7-[2α-hydroxy-5-(3-hydroxy-3-methyl-1-octenyl)cyclopentyl]-5-heptenoic acid, described in the copending U.S. application Ser. No. 351,381, filed Apr. 16, 1973, via the intermediate hemiacetal of formula 13, hexahydro-2-hydroxy-4-{3-[(tetrahydropyran-2-yl)oxy]-1-octenyl}-2H-cyclopenta[b]furan, $\nu_{max}^{film}$ 3350 cm$^{-1}$.

Likewise, the use of 2α-hydroxy-5-{3-[(tetrahydropyran-2-yl)oxy]octyl}cyclopentaneacetic acid γ-lactone, described in Example 142, gives cis-7-[2α-hydroxy-5-(3-hydroxyoctyl)cyclopentyl]-5-heptenoic acid, nmr (CDCl$_3$) δ 9.0 (t, J = 5, 3H), 3.65 (m, 1H), 4.25 (m, 1H), 4.9 (s, 3H), 5.5 (m, 2H), via the intermediate hemiacetal of formula 10, hexahydro-2-hydroxy-4-[3-(dimethyl-tert-butyl)octyl]-2H-cyclopenta[b]furan, $\nu_{max}^{film}$ 3360 cm$^{-1}$.

Likewise, the use of 2α-hydroxy-5-(3-hydroxy-3-methyloctyl)-cyclopentaneacetic acid γ-lactone, described in Example 149, gives cis-7-[2α-hydroxy-5-(3-hydroxy-3-methyloctyl)cyclopentyl]-5-heptenoic acid, nmr (CDCl$_3$) δ 0.9 (t, J = 5, 3H), 1.2 (s, 3H), 1.5 (s, 2H), 4.2 (m, 1H), 5.5 (m, 2H), via the intermediate hemiacetal of formula 10, hexahydro-2-hydroxy-4-[(3-hydroxy-3-methyloctyl]-2H-cyclopenta[b]furan, $\nu_{max}^{film}$ 3355 cm$^{-1}$.

Likewise, the use of 2α-hydroxy-5-(3-hydroxy-4,4-dimethyloctyl)cyclopentaneacetic acid γ-lactone, described in Example 142, gives cis-7-[2α-hydroxy-5-(3-hydroxy-4,4-dimethyloctyl)cyclopentyl]-5-heptenoic acid, via the intermediate hemiacetal of formula 10, hexahydro-2-hydroxy-4-{3-(dimethyl-tert-butylsilyloxy)-4,4-dimethyloctyl}-2H-cyclopenta-[b]furan, $\nu_{max}^{film}$ 3350 cm$^{-1}$ and the corresponding dimethyl tert-butyl ether of cis-7-[2α-hydroxy-5-(3-hydroxy-4,4-dimethyloctyl)cyclopentyl]-5-heptenoic acid has $\nu_{max}^{film}$ 3350, 3260 cm$^{-1}$.

Further examples of the compound of formula 11 are listed in Table XII. In each case the requisite starting material of formula 9 is noted by the example in which it is prepared.

TABLE XII

| EXAMPLE | NO. OF EXAMPLE IN WHICH STARTING MATERIAL OF FORMULA 9 IS PREPARED | WITTIG REAGENT OF FORMULA $\bigcirc_3$-$\overset{+}{P}$=CH-(CH$_2$)$_m$COOR$^7$ Br$^-$ | | PRODUCT: |
|---|---|---|---|---|
| | | m | R$^7$ | |
| 176 | 143 | 3 | H | cis-7-[2α-hydroxy-5-(3-hydroxy-4-propylheptyl)-cyclopentyl]-5-heptenoic acid |
| 177 | 144 | 2 | H | cis-6-[2α-hydroxy-5-(4-ethyl-3-hydroxynonyl)-cyclopentyl]-4-hexenoic acid |
| 178 | 145 | 1 | H | cis-5-[2α-hydrocy-5-(4,4-dimethyl-3-hydroxy-1-decyl)cyclopentyl]-3-pentenoic acid |
| 179 | 146 | 2 | CH$_3$ | cis-6-[2α-hydroxy-5-(4-ethyl-3-hydroxy-4-methyldecyl)cyclopentyl]-4-hexenoic acid methyl ester |
| 180 | 147 | 3 | H | cis-7-[2α-hydroxy-5-(3-hydroxy-4-methyl-4-propylheptyl)cyclopentyl]-5-heptenoic acid |
| 181 | 148 | 2 | C$_2$H$_5$ | cis-6-[2α-hydroxy-5-(3-hydroxy-4,4-dipropylnonyl)-cyclopentyl]-4-hexenoic acid ethyl ester |
| 182 | 150 | 3 | H | cis-7-[2α-hydroxy-5-(4-ethyl-3-hydroxy-3-methylheptyl)cyclopentyl]-5-heptenoic acid |
| 183 | 151 | 2 | n-C$_3$H$_7$ | cis-6-[2α-hydrocy-5-(3- |

TABLE XII-continued

WITTIG REAGENT OF FORMULA $$\underset{(CH_2)_m COOR^7}{\bigcirc}_3-\overset{\pm}{P}=CH- \quad Br^-$$

| EXAMPLE | NO. OF EXAMPLE IN WHICH STARTING MATERIAL OF FORMULA 9 IS PREPARED | m | R⁷ | PRODUCT: |
|---|---|---|---|---|
| 184 | 152 | 1 | H | ethyl-3-hydroxy-4-propylnonyl)cyclopentyl]-4-hexenoic acid propyl ester cis-5-[2α-hydroxy-5-(4-ethyl-3-hydroxy-3-propyldecyl)cyclopentyl]-3-pentenoic acid |
| 185 | 153 | 2 | CH₃ | cis-6-[2α-hydroxy-5-(3-ethyl-3-hydroxy-4-methylheptyl)cyclopentyl]-4-hexenoic acid methyl ester |
| 186 | 154 | 3 | H | cis-7-[2α-hydrocy-5-(3-hydroxy-3,4-dimethylnonyl)cyclopentyl]-5-hexenoic acid |
| 187 | 155 | 2 | H | cis-6-[2α-hydroxy-5-(3,4-diethyl-3-hydroxyoctyl)-cyclopentyl]-4-hexenoic acid |
| 188 | 156 | 1 | CH₃ | cis-5-[2α-hydroxy-5-(3-hydroxy-4-methyldecyl)-cyclopentyl]-3-pentenoic acid methyl ester |

EXAMPLE 189 cis-7-[2-(3-hydroxy-4,4-dimethyloctyl)-5-oxocyclopentyl]-5-heptenoic acid (11; $R^2$, $R^6$ and $R^7$ = H, $R^4$ and $R^5$ = $CH_3$, X and Y = O,Z = $CH_2CH_2$, m = 3 and n = 3)

To a solution of cis-7-{2α-hydroxy-5-[3-(dimethyl-tert-butylsilyloxy)-4,4-dimethyloctyl]cyclopentyl}-5-heptenoic acid (0.817 g), described in Example 175, in acetone (10 ml), cooled to −10°, 0.75 ml of Jones' reagent [chromic acid in acetone containing a trace of sulphuric acid, see E. R. H. Jones, et al., *J. Chem. Soc.*, 2548 (1953)] is added. After stirring for 10 minutes the excess reagent is destroyed with methanol. The reaction mixture is diluted with water and extracted with ether. The extract is washed with water, dried ($Na_2SO_4$) and the solvent removed to yield cis-7-{2-[3-(dimethyl-tert-butylsilyloxy)-4,4-dimethyloctyl]-5-oxocyclopentyl}-5-heptenoic acid, $\nu_{max}^{film}$ 1730, 1710 $cm^{-1}$.

The latter compound is deprotected by treatment with p-toluenesulfonic acid in aqueous methanol according to the procedure of Example 175 to give the title compound $\nu_{max}^{film}$ 3470, 1730, 1710 $cm^{-1}$.

In the same manner but replacing cis-7- {2α-hydroxy-5-[3-(dimethyl isopropylsilyloxy)-4,4-dimethyloctyl]cyclopentyl}-5- heptenoic acid by the appropriate compound of formula 11 in which X and Y are hydroxy and hydrogen, respectively, other corresponding compounds of formula 11 in which X and Y are oxo are obtained. Note protection of the hydroxyl on the side chain is not required when it is a tertiary alcohol (i.e., $R^6$ = lower alkyl).

For example, in the same manner, but replacing cis-7- 2α-hydroxy-5-[3-(dimethylisopropylsilyloxy)-4,4-dimethyloctyl]cyclopentyl -5-heptenoic acid, with cis-7- 2α-hydroxy-5-[3-(dimethylisopropylsilyloxy)octyl]-cyclopentyl -5-heptenoic acid, described in Example 175, cis-7-[2-(3-hydroxyoctyl)-5-oxocyclopentyl]-5-heptenoic acid, nmr ($CDCl_3$) δ 0.9 (t, J = 5, 3H), 3.7 (m, 1H), 5.42 (m, 2H), 6.6 (s, 2H), is obtained.

Likewise, replacement with cis-7-[2α-hydroxy-5-(3-hydroxy-3-methyloctyl)cyclopentyl]-5-heptenoic acid, described in Example 175 gives cis-7-[2-(3-hydroxy-3-methyloctyl)-5-oxocyclopentyl]-5-heptenoic acid, nmr ($CDCl_3$), δ 0.9 (t, J = 5, 3H), 5.42 (m, 2H), 6.5 (s, 2H).

Furthermore if desired a compound of formula 11 ($R^6$ = H) may be separated into its two epimers with respect to the asymmetric carbon atom bearing the hydroxy group. This separation is effected preferably by converting the aforementioned compound to its corresponding methyl ester using methanol in the presence of a acid catalyst, for example, 2% perchloric acid, and subjecting the ester to chromatography on $S.O_2$ use benzene-ethyl acetate (9:1) as eluant. In this manner the epimers are separated. These isomers are arbitrarily designated as isomers A (least polar isomer) and isomer B (more polar isomer); the polarity being determined by the order in which they are eluted. Thereafter the epimers may be hydrolyzed with 5% sodium hydroxide in aqueous methanol for 15 minutes at 30° to 40° to give the corresponding acid.

For example, by the preceding method the epimers of the title compound are obtained, Isomer A has $\nu_{max}^{film}$ broad hydroxyl, 1725 to 1730 $cm^{-1}$, and Isomer B has $\nu_{max}^{film}$ broad hydroxyl, 1725 to 1730 $cm^{-1}$.

The corresponding methyl esters of the peceding Isomers A and B have the following characteristics:

Isomer A, a racemate of methyl cis-7-[2-(3-hydroxy-4,4-dimethyloctyl)-5-oxocyclopentyl]-5-heptenoate, has Rf of about 0.47 on thin layer plates of silica gel when using ethyl acetate-benzene (1:4) as the mobile phase.

Isomer B, a second racemate of methyl cis-7-[2-(3-hydroxy-4,4-dimethyloctyl)-5-oxocyclopentyl]-5-heptenoate, has Rf of about 0.37 on thin layer plates of

We claim:
1. A compound of the formula

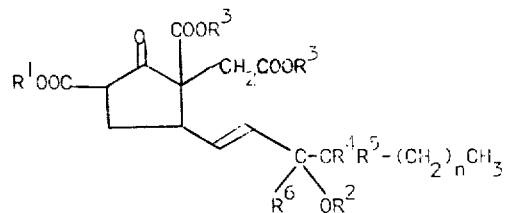

in which $R^1$ and $R^3$ each are lower alkyl, $R^2$ is hydrogen or a hydroxy protecting radical selected from the group consisting of acetals, tri (lower) alkylsilyl or tert-butyl, $R^4$, $R^5$ and $R^6$ each are hydrogen or lower alkyl and $n$ is an integer from two to five, with the proviso that at least one of $R^4$, $R^5$ or $R^6$ is hydrogen.

2. Dimethyl trans-1-(Carbomethoxymethyl)-5-(3-hydroxy-1-octenyl)-2-oxo-1,3-cyclopentanedicarboxylate, as claimed in claim 1.

3. The compound of claim 2 in the form of its tetrahydropyran-2-yl ether, as claimed in claim 1.

4. Dimethyl trans-1-(Carboethoxymethyl)-5-(3-hydroxy-3-methyl-1-octenyl)-2-oxo-1,3-cyclopentanedicarboxylate, as claimed in claim 1.

5. Dimethyl trans-1-(Carboxymethoxymethyl)-5-(3-hydroxy-4,4-dimethyl-1-octenyl)-2-oxo-1,3-cyclopentanedicarboxylate, as claimed in claim 1.

* * * * *